(12) United States Patent
Maine

(10) Patent No.: US 6,177,241 B1
(45) Date of Patent: Jan. 23, 2001

(54) USE OF PEPTIDES TO IMPROVE SPECIFICITY OF AN IMMUNOASSAY FOR THE DETECTION OF CYTOMEGALOVIRUS SPECIFIC IGM ANTIBODY

(75) Inventor: Gregory T. Maine, Gurnee, IL (US)

(73) Assignee: Abbott Laboratories, Abbott Park, IL (US)

( * ) Notice: Under 35 U.S.C. 154(b), the term of this patent shall be extended for 0 days.

(21) Appl. No.: 08/935,009

(22) Filed: Sep. 22, 1997

(51) Int. Cl.[7] .............................. C12Q 1/70; G01N 33/53
(52) U.S. Cl. .............................. 435/5; 435/7.6; 435/7.92; 435/69.3; 435/71.1; 435/252.33; 435/254.23; 435/320.1; 530/350; 436/513; 436/518; 436/531; 436/534; 436/548
(58) Field of Search .............................. 435/5, 7.6, 7.92, 435/69.3, 71.1, 252.33, 254.23, 320.1; 530/350; 436/518, 531, 534, 573

(56) References Cited

U.S. PATENT DOCUMENTS

| 5,116,725 | * | 5/1992 | Vaughan | 435/5 |
| 5,122,448 | * | 6/1992 | Vaughan | 435/5 |
| 5,244,630 | * | 9/1993 | Khalil | 422/52 |

FOREIGN PATENT DOCUMENTS

9601321 * 1/1996 (WO) .

OTHER PUBLICATIONS

Vornhagen et al. J. Clin. Microbiol. 32:981–986, 1994.*
Landini et al. J. Clin. Microbiol. 32:1375–1379, 1990.*
Ripalti, et al (1994) J Clin Microb vol 32 (2) pp. 358–363.*

* cited by examiner

Primary Examiner—Donna Wortman
Assistant Examiner—Mary K. Zeman
(74) Attorney, Agent, or Firm—David L. Weinstein

(57) ABSTRACT

This invention provides a method, a reagent, and a kit for detecting herpesvirus-specific IgM antibodies indicative of recent infection while preventing detection of low levels of herpesvirus-specific IgM antibodies present in individuals of low risk. The invention also provides a reagent for use in detecting herpesvirus-specific IgM antibodies indicative of recent infection while preventing detection of low levels of herpesvirus-specific IgM antibodies present in individuals of low risk.

The method of this invention comprises the steps of:

(a) providing a solid phase containing at least a portion of a herpesvirus antigen;

(b) introducing a patient specimen to the solid phase of step (a);

(c) introducing at least one peptide capable of specifically binding IgM antibodies to herpesvirus to the solid phase of step (a);

d) allowing IgM antibodies to herpesvirus to specifically bind to the portion of antigen of herpesvirus and the peptide capable of specifically binding IgM antibodies to herpesvirus to the solid phase; and (e) determining the level of IgM antibodies to herpesvirus in the patient specimen.

30 Claims, 19 Drawing Sheets

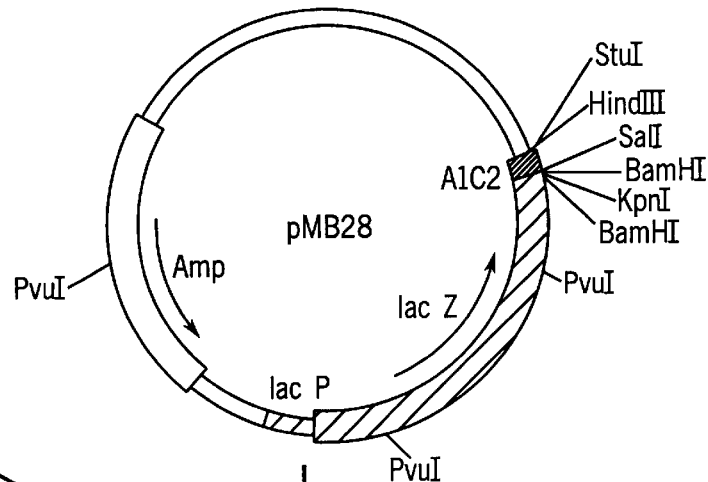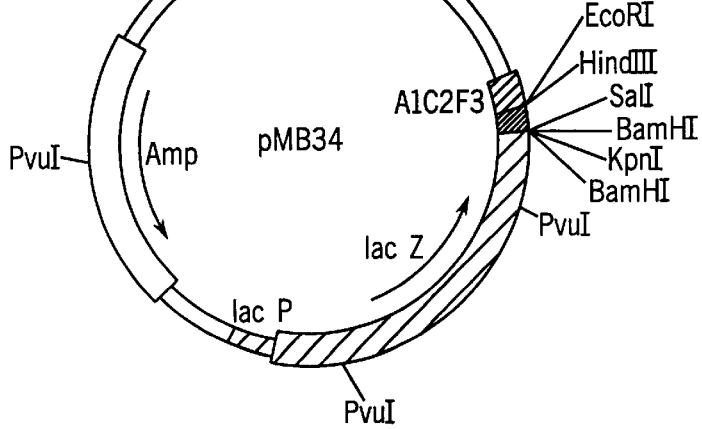
FIG. 4

Table 1
Comparison between IgG detection by ELISA with whole CMV or by recombinant ELISA with individual fusion proteins

| ELISA (IgG) with whole CMV | | ELISA (IgG) with the following fusion proteins: | | | | | | | | | |
|---|---|---|---|---|---|---|---|---|---|---|---|
| | | F3 | | A1C2 | | A1C2/F3 | | H10 | | A1C2/F3/H10 | |
| N | Mean Titre (Range) | N. Positives | Mean Titre (Range) | N. Positives | Mean Titre (Range) | N. Positives | Mean Titre (Range) | N. Positives | Mean Titre (Range) | N. Positives | Mean Titre (Range) |
| 28 | 291 (242–330) | 19 | 75 (17–180) | 10 | 41 (17–43) | 20 | 172 (40–490) | 19 | 214 (168–501) | 27 | 176 (140–641) |
| 40 | 576 (434–705) | 40 | 434 (53–2079) | 22 | 110 (12–440) | 40 | 825 (230–2209) | 39 | 611 (206–1038) | 40 | 880 (120–2160) |
| 40 | 1161 (690–2138) | 38 | 796 (50–2461) | 22 | 114 (25–2750) | 38 | 805 (50–2351) | 40 | 758 (300–2120) | 40 | 940 (120–2405) |
| 108 | TOTAL | 98 (90.7%) | — | 54 (50%) | — | 97 (89.8%) | — | 98 (90.7%) | — | 107 (99.1%) | — |
| 14 | 0.18 (0.2–5) | 0 | — | 0 | — | 0 | — | 0 | — | 0 | — |

FIG. 6

TABLE 2

Comparison between IgM detection by ELISA with whole CMV or by recombinant ELISA with individual fusion proteins

| ELISA (IgM) with whole CMV | | ELISA (IgM) with the following fusion proteins: | | | | | | | | | |
|---|---|---|---|---|---|---|---|---|---|---|---|
| | | F3 | | A1C2 | | A1C2 / F3 | | H10 | | A1C2 / F3 / H10 | |
| N. | Mean Titre (Range) | N. Positives | Mean Titre (Range) | N. Positives | Mean Titre (Range) | N. Positives | Mean Titre (Range) | N. Positives | Mean Titre (Range) | N. Positives | Mean Titre (Range) |
| 20 | 294 (242-389) | 10 | 521 (232-1171) | 10 | 317 (85-612) | 14 | 797 (210-1417) | 19 | 578 (432-724) | 20 | 517 (386-815) |
| 24 | 516 (210-2297) | 18 | 1090 (210-2297) | 16 | 467 (143-1141) | 22 | 1278 (370-2561) | 23 | 887 (209-2270) | 24 | 767 (298-1973) |
| 20 | 1341 (881-2000) | 16 | 1163 (451-2339) | 14 | 1021 (202-2260) | 16 | 1707 (521-2249) | 20 | 1065 (579-2471) | 20 | 1121 (421-2243) |
| 64 | TOTAL positives | 44 (68.75%) | | 40 (62.5%) | | 52 (81.25%) | | 62 (96.87%) | | 64 (100%) | |
| 5 | 27 (1-56) | 0 | — | 0 | — | 0 | — | 0 | — | 0 | — |

FIG. 7

```
                    SalI
          MluI        MluI
           ▼     ▼  ▼
      CCCGCGCGCTACGCGTCGACGCGTCTGCCC
      ProAlaArgTyrAlaSerThrArgLeuPro
```

FIG. 14B

```
      5' CGCGAGCT 3'
      3'     TCGAGCGC 5'
```

FIG. 14C

```
      CCCGCGCGCTACGCGACGTCGCGTCTGCCC
      ProAlaArgTyrAlaThrSerArgLeuPro
```

FIG. 14D

USE OF PEPTIDES TO IMPROVE SPECIFICITY OF AN IMMUNOASSAY FOR THE DETECTION OF CYTOMEGALOVIRUS SPECIFIC IGM ANTIBODY

BACKGROUND OF THE INVENTION

1. Field of the Invention

This invention relates to the use of peptides derived from herpesvirus proteins to improve the specificity of enzyme immunoassays for the detection of herpesvirus-specific IgM antibody.

2. Discussion of the Art

Diagnosis of herpesvirus infection is typically accomplished by serological methods, i.e., demonstration of the appearance of antibodies to herpesvirus antigens in a previously seronegative subject. Herpesvirus IgM antibodies can be a sensitive and specific indicator of primary herpesvirus infection in immunocompetent subjects. However, its detection varies widely because of low levels of IgM antibodies produced in some patients.

A problem with assays utilizing herpesvirus antigens for detecting herpesvirus-specific IgM antibodies is that the assays are so sensitive that low levels of herpesvirus-specific IgM antibodies that are present in individuals of low risk are frequently detected. In other words, these assays indicate too many false positive results. The diagnosis of recent herpesvirus infection, e.g., 0 to 8 months, is questionable because the low level of IgM antibodies present in individuals experiencing an asymptomatic reactivation from a previous herpesvirus infection may be detected. If the level of herpesvirus antigen in the reagent is reduced to improve the specificity of the assay, the sensitivity of the assay is also reduced. In other words, it is undesirable to obtain a positive result in asymptomatic patients who have not had an infection within the previous eight months. Accordingly, it would be desirable to provide an assay for herpesvirus that not only detects IgM antibodies indicative of recent infection, but that also fails to detect IgM antibodies that are not indicative of recent infection.

Human Cytomegalovirus (HCMV) is a ubiquitous herpesvirus in human beings. It is rarely pathogenic in healthy adults but is associated with several diseases in immunocompromised individuals (such as persons infected with HIV and transplant recipients). Furthermore, HCMV is the most common cause of congenital infection in humans. Intrauterine primary infections are second only to Down's syndrome as a known cause of mental retardation. Less severe complications result from secondary infections. Because infections are either asymptomatic or accompanied by symptoms that are not specific of HCMV (such as fever and leukopenia), laboratory techniques are the sole means of diagnosing acute HCMV infection. Diagnosis of HCMV infection can be obtained by direct demonstration of the virus or virus components in pathological materials or indirectly through serology. Diagnosis of primary HCMV infection is accomplished exclusively by serological methods, i.e. demonstration of the appearance of antibodies to HCMV in a previously seronegative subject. HCMV-specific IgM is a sensitive and specific indicator of primary HCMV infection in immunocompetent subjects, and it is very often produced during active viral reactivation in transplant recipients. However its detection varies widely and a very poor agreement has been found among the results obtained with different commercial kits.

European Patent Application 262531 discloses immunogenic portions of HCMV structural phosphoprotein of 150 kD, encoded by the gene localized in the Hind III-Y/N fragment of the viral genome; according to that European Patent Application, such immunogenic portions of pp150 are encoded, in particular, by an EcoRI-PstI fragment of approximately 1.5 kb, localized inside the region of EcoRI-Y fragment from HCMV genome of AD169 strain. Subsequent and more exhaustive studies have however shown the disclosure of European Patent Application 262531 to be incorrect, in that protein pp150 is shown to be encoded by UL32, is shown to have a length much greater than 1.5 kb and, finally, is shown to be quite outside any such EcoRI-PstI fragment, as may be defined within the EcoRI-Y fragment of the AD169 strain. Furthermore, the EcoRI-Y fragment is wholly outside of Hind III-Y/N fragment.

According to U.S. Ser. No. 08/765,856, filed Dec. 27, 1996 (hereinafter "U.S. Ser. No. 08/765,856"), there is a correlation between the immunogenic properties shown by the proteic material referred to in the aforementioned European patent application (which, however, providing an incorrect identification of the polypeptide, causes it to remain substantially undetermined) and the inclusion into the peptide of epitope A1C2, encoded bag UL32 nucleotides 1783 to 1842, running 5'→43', i.e., of the region corresponding to amino acids 595 to 614 of ppUL32, whose identification is posterior (Novak J. P. et al. 1991. Mapping of serologically relevant regions of human cytomegalovirus phosphoprotein pp150 using synthetic peptides. J. Gen. Virol. 72; 1409–1413).

U.S. Ser. No. 08/765,856 discloses a recombinant proteic material, in particular, a fusion protein, capable of binding by immunoreaction with antibodies produced against human Cytomegalovirus, in particular, both IgM and IgG, capable of being used as an antigen for detecting such antibodies in the relevant serologic tests, with substantially the same efficacy as the virus and/or of infected cell lyses. U.S. Ser. No. 08/765,856 further discloses diagnostic reagents and kits derived from that proteic material.

U.S. Ser. No. 08/765,856 discloses recombinant antigens, in particular fusion proteins, to detect Cytomegalovirus-specific IgM in human sera by enzyme immunoassay. U.S. Ser. No. 08/765,856 further discloses diagnostic, reagents and kits derived from those proteic materials.

According to U.S. Ser. No. 08/765,856, there is provided a recombinant proteic material, capable of binding with antibodies against human Cytomegalovirus (HCMV), characterized in that it consists of a fusion protein comprising a first region, carrying at least part of the sequence between aa 202 and aa 434, inclusive, read in 5'→3' direction, of protein pp52, a second region, carrying at least a part of the sequence between aa 1006 and aa 1048, inclusive, read in 5'→3' direction, of pp150, and a third region, carrying at least a part of the sequence between aa 595 and 614 inclusive, in 5'→3' direction, of pp150. These regions are capable of being variably arranged with respect to one another within the fusion protein.

These regions preferably comprise the sequences of pp52 and pp150 in full, and, according to a preferred embodiment, a fusion protein according to U.S. Ser. No. 08/765,856 comprises in a sequential manner, running 5'→3': the first region, immediately downstream wherefrom there is placed the third region, and then the second region, downstream from the third region, a bridge sequence being inserted between the third and the second regions. The bridge sequence consists, running 5'→3', of the following series of aminoacids: lys leut gln glu phe. See SEQ ID NO: 7.

U.S. Ser. No. 08/765,856 further provides for a reagent for diagnosing HCMV infection by serological methods comprising a fusion protein as defined previously. In particular, the diagnostic reagent comprises a fusion protein, whereof at least part of the amino acids is encoded by the nucleotide sequence shown in the sequence listing as SEQ ID NO: 1, read from nucleotide 001 to nucleotide 900.

U.S. Ser. No. 08/765,856 also relates to diagnostic reagents for direct detection of HCMV through serology, comprising at least one monospecific polyclonal serum, or monoclonal antibodies (MaB), directed against the fusion protein.

According to another aspect of U.S. Ser. No. 081765,856, there is provided a mixture of recombinant antigens to detect Cytomegalovirus-specific IgM in human sera by enzyme immunoassay, the mixture being characterized in that it includes, in combination:

(i) a first fusion protein comprising: a first region, carrying an amino acid sequence (H10) corresponding to at least part of the sequence between a2L 202 and aa 434, inclusive, read in 5'→3' direction, of viral protein pp52; a second region, carrying an amino acid sequence (F3) corresponding to at least part of the sequence between aa 1006 to aa 1048, inclusive, read in 5'→3' direction, of viral protein pp150; and a third region, carrying an amino acid sequence (A1C2) corresponding to at least part of the sequence between aa 595 and aa 614 inclusive, read in 5'→3' direction, of the same viral protein pp150; which regions are capable of being variably arranged with respect to one another within the first fusion protein;

(ii) a second fusion protein comprising an immunogen region consisting in a sequence of amino acids corresponding to at least part of the sequence between aa 297 to aa 510, inclusive, read in 5'→3' direction, of the major matrix protein pp65 encoded by the viral gene UL83; and (iii) a third fusion protein comprising an immunogen region consisting in a sequence of amino acids corresponding to at least part of the sequence between aa 117 to aa 373, read in 5'→3' direction, of the viral assembly protein pp38 encoded by the viral gene UL80a.

In particular, the aforementioned regions include the amino acid sequences of pp52, pp150, pp65, and pp38 in full, fused together with protein CKS or at least a part thereof.

Finally, U.S. Ser. No. 08/765,856 relates to the use of a mixture of mono- and poly- epitope fusion proteins to detect Cytomegalovirus-specific IgM in human sera by enzyme immunoassay, the mixture being characterized in that it includes, in combination:

(i) a first fusion protein comprising: a first region, carrying an amino acid sequence (H10) corresponding to at least part of the sequence between aa 202 and aa 434, inclusive, read in 5'→3' direction, of viral protein pp52; a second region, carrying an amino acid sequence (F3) corresponding to at least part of the sequence between aa 1006 to aa 1048, inclusive, read in 5'→3' direction, of viral pp150; and a third region, carrying an amino acid sequence (A1C2) corresponding to at least part of the sequence between aa 595 and 614 inclusive, read in 5'→3' direction, of the same viral protein pp150; which regions are capable of being variably arranged with respect to one another within the first fusion protein;

(ii) a second fusion protein comprising an immunogen region consisting in a sequence of amino acids corresponding to at least part of the sequence between aa 297 to aa 510, inclusive, read in 5'→3' direction, of the major matrix protein pp65 encoded by the viral gene UL83; and (iii) a third fusion protein comprising an immunogen region consisting in a sequence of amino acids corresponding to at least part of the sequence between aa 117 to aa 373, read in 5'→3' direction, of the viral assembly protein pp38 encoded by the viral gene UL80a.

U.S. Ser. No. 08/765,856 further relates to the use of the above mixture of fusion proteins to produce a diagnostic kit to detect Cytomegalovirus. specific IgM in human sera by enzyme immunoassay.

The fusion protein, H10/A1C2/F3, was found to have a much higher IgG and IgM reactivity than that obtainable by properly combining in one single test kit the proteins containing the three distinct epitopes. A synergic effect, therefore, takes place, probably owing to the fact that, arranging such epitopes, as are normally far off, close to one another on the same viral protein (A1C2 and F3 of ppUL32, for instance) or even on different proteins (such as H10 of ppUL44), causes conformational epitopes, likely to be present in the original complete viral proteins and/or on the virions, to be "mimicked".

The new fusion protein, comprising the aforementioned sequences, has indeed proven to be as active as the purified virions in binding with IgG and IgM of infected subjects, thus finally allowing production of a standardized antigen, both as to quality and as to quantity, capable of actually replacing purified virions and/or infected cells in the preparation of diagnostic kits for HCMV infection serodiagnosis. Clearly, the previously described epitopes may be included into the new fusion protein as according to the invention in U.S. Ser. No. 08/765,856 in the order of sequence SEQ ID NO: 2, or else in any other sequence, also allowing for bridge sequences to be inserted between them, like that corresponding to nucleotides 757 to 771 of SEQ ID NO: 1.

According to a further aspect of the invention of U.S. Ser. No. 08/765,856, and starting from the results described above, the poly-epitope protein according to the first aspect of the invention has been further studied arranging the said regions in a different way and combining the recombinant material, expressed fused together with protein CKS, with immunogenic regions of other HCMV proteins, so obtaining a mixture of fusion proteins highly effective against IgM.

The fusion proteins according to the invention of U.S. Ser. No. 08/765,856 can be used alone or mixed together, for direct preparation of diagnostic reagents for serological detection of HCMV-specific antibodies, in that their ability of efficiently binding anti-HCMV IgM, in particular those produced during a primary phase of the infection, is substantially 100%. Such reagents may comprise the mixture of fusion proteins according to the invention of U.S. Ser. No. 08/765,856, eventually in combination with other HCMV antigens, or else more complex fusion proteins, including the immunogenic sequences repeated many times and anyway in combination with one another.

The proteic materials represented by the fusion proteins according to the invention of U.S. Ser. No. 08/765,856 can be further used for the preparation, by means of known techniques, of diagnostic reagents for serological detection of human Cytomegalovirus and/or antigens for the detection thereof represented by specific polygonal sera, or by monoclonal antibodies (MaB) directed against the proteins of the invention of U.S. Ser. No. 08/765,856 and obtained via a number of different methods.

These diagnostic reagents, containing the proteins according to the invention of U.S. Ser. No. 08/765,856, can be used, in turn, for the production of diagnostic kits for the demonstration, by serological methods, of the appearance of antibodies to human Cytomegalovirus (HCMV), wherein the reagent is adsorbed on nitrocellulose paper (blotting). Finally, the proteins according to the invention of U.S. Ser. No. 08/765,856 can be used, after being purified, in ELISA assays, latex agglutination tests, RIA, as well as in all known serological screening methods for the presence of HCMV-specific IgG and IgM, both manual and partially or completely automated.

A problem with the assay utilizing the fusion protein H10/A1C2/F3 is that it is so sensitive that low levels of HCMV-specific IgM antibodies that are present in individuals of low risk are frequently detected. In other words, the assay indicates too many false positive results. The diagnosis of recent HCMV infection, e.g., 0 to 8 months, is questionable because the low level of IgM antibody present in individuals experiencing an asymptomatic reactivation from a previous HCMV infection may be detected. If the level of fusion protein H10/A1C2/F3 in the reagent is reduced to improve the specificity of the assay, the sensitivity of the assay is also reduced. In other words, it is undesirable to obtain a positive result in asymptomatic patients who have not had an infection within the previous eight months. Accordingly, it would be desirable to provide an assay for HCMV that not only detects IgM antibody indicative of recent infection, but that also fails to detect IgM antibody that is not indicative of recent infection.

SUMMARY OF THE INVENTION

In one aspect, this invention provides a method for detecting herpesvirus-specific IgM antibodies indicative of recent infection while preventing detection of low levels of herpesvirus-specific IgM antibodies present in individuals of low risk. The invention also provides a reagent for use in detecting herpesvirus-specific IgM antibodies indicative of recent infection while preventing detection of low levels of herpesvirus-specific IgM antibodies present in individuals of low risk.

The method of this invention comprises the steps of:
(a) providing a solid phase containing at least a portion of a herpesvirus antigen;
(b) introducing a patient specimen to the solid phase of step (a);
(c) introducing at least one peptide capable of specifically binding IgM antibodies to herpesvirus to the solid phase of step (a);
(d) allowing IgM antibodies to herpesvirus to specifically bind to the portion of antigen of herpesvirus and the peptide capable of specifically binding IgM antibodies to herpesvirus; and
(e) determining the level of IgM antibodies to herpesvirus in the patient specimen.

In one embodiment of the invention, the solid phase is a microparticle. In this embodiment, microparticles coated with the herpesvirus antigen are suspended in a diluent containing peptide capable of specifically binding IgM antibodies to herpesvirus. The patient specimen is diluted with buffer and then incubated with the coated microparticles suspended in the diluent. Herpes virus-specific IgM antibodies to herpesvirus antigen bind to the microparticles (solid phase) and peptide capable of specifically binding IgM antibodies to herpesvirus (liquid phase). The solid and liquid phases are then separated and only IgM antibodies bound to the microparticles are detected with a human IgM specific conjugate.

In another embodiment of the invention, the solid phase is a strip of material. In this embodiment, a nitrocellulose strip is impregnated with herpesvirus antigen purified from the herpesvirus. The patient specimen is diluted with buffer containing the peptide capable of specifically binding IgM antibodies to herpesvirus. The diluted sample containing the peptide capable of specifically binding IgM antibodies to herpesvirus is then applied to the nitrocellulose strip. Herpes virus-specific IgM antibodies to herpesvirus antigen bind to the nitrocellulose (solid phase) and peptide capable of specifically binding IgM antibodies to herpesvirus (liquid phase). The solid and liquid phases are then separated and only IgM antibodies bound to the nitrocellulose are detected with human IgM specific conjugate.

A reagent suitable for use in one embodiment of this invention comprises a solution containing microparticles coated with at least a portion of herpesvirus antigen, suspended in a diluent containing at least one peptide capable of specifically binding IgM antibodies to herpesvirus antigen. A reagent suitable for use in another embodiment of this invention comprises a sample diluent containing at least one peptide capable of specifically binding IgM antibodies to herpesvirus antigen.

A kit suitable for use in this invention on an automated instrument comprises:
(a) microparticles coated with at least a portion of herpesvirus antigen, preferably suspended in a diluent containing at least one peptide capable of specifically binding IgM antibodies to herpesvirus antigen;
(b) IgM conjugate in a diluent; and
(c) buffered diluent containing a blocking agent.

In the method, the reagent, and the kit, the amount of the at least one peptide capable of specifically binding IgM antibodies to herpesvirus must be sufficient to bind low levels of herpesvirus-specific IgM antibody present in patient specimens not indicative of acute or recent herpesvirus infection, yet, not so great that the at least one peptide capable of specifically binding IgM antibodies to herpesvirus binds medium to high levels of herpesvirus-specific IgM antibody present in patient specimens indicative of acute or recent herpesvirus infection.

In one specific aspect, this invention provides a method for detecting HCMV-specific IgM antibodies indicative of recent infection while preventing detection of low levels of HCMV-specific IgM antibodies present in individuals ELF low risk. The invention also provides a reagent for use in detecting HCMV-specific IgM antibodies indicative of recent infection while preventing detection of low levels of HCMV-specific IgM antibodies present in individuals of low risk.

The method of this aspect of the invention comprises the steps of:
(a) providing a solid phase containing at least a portion of human cytomegalovirus, preferably the pp150 protein (hereinafter "pp 150");
(b) introducing a patient specimen to the solid phase of step (a);
(c) introducing at least one peptide capable of specifically binding IgM antibodies to human cytomegalovirus to the solid phase of step (a);
(d) allowing IgM antibodies to human cytomegalovirus to specifically bind to the portion of human cytomegalovirus, preferably pp150, and the peptide capable of specifically binding IgM antibodies to human cytomegalovirus; and
(e), determining the level of IgM antibodies to human cytomegalovirus in the patient specimen.

In a preferred embodiment of this aspect of the invention, the method of this invention involves the steps of:

(a) providing a solid phase containing the fusion protein H10/A1C2/F3 of pp150 of human cytomegalovirus;

(b) introducing a patient specimen to the solid phase of step (a);

(c) introducing peptides A1C2 and F3 of pp150 of human cytomegalovirus to the solid phase of step (a);

(d) allowing IgM antibodies to human cytomegalovirus to specifically bind to the fusion protein H10/A1C2/F3 and the peptides A1C2 and F3; and (e) determining the level of IgM antibodies to human cytomegalovirus in the patient sample.

In one preferred embodiment of the invention, the solid phase is a microparticle. In this preferred embodiment, microparticles coated with the fusion protein H10/A1C2/F3 are suspended in a buffered sucrose/calf serum diluent containing the peptides A1C2 and F3. The biological sample is diluted with buffer and then incubated with the coated microparticles suspended in the buffered sucrose/calf serum/peptide diluent. HCMV-specific IgM antibodies to pp150 bind to the microparticles (solid phase) and peptides (liquid phase). The solid and liquid phases are then separated and only IgM antibodies bound to the microparticles are detected with a goat anti-human IgM specific conjugate.

In another preferred embodiment of the invention, the solid phase is a strip of material. In this embodiment, a nitrocellulose strip is impregnated with pp150 purified from the virus and fusion protein A1C2/F3. The biological sample is diluted with buffer containing the peptides A1C2 and F3. The diluted sample containing the peptides is then applied to the nitrocellulose strip. HCMV-specific IgM antibodies to pp150 bind to the nitrocellulose (solid phase) and peptides (liquid phase). The solid and liquid phases are then separated and only IgM antibodies bound to the nitrocellulose are detected with goat anti-human IgM specific conjugate The foregoing embodiment is described in PCT/US 97/13942, incorporated herein by reference.

A reagent suitable for use in one embodiment of this invention comprises a solution containing microparticles coated with at least a portion of human cytomegalovirus, preferably pp150, more preferably the fusion protein H10/A1C2/F3, suspended in a diluent containing at least one peptide capable of specifically binding IgM antibodies to human cytomegalovirus, preferably the peptides A1C2 and F3. A reagent suitable for use in another embodiment of this invention comprises a sample diluent containing at least one peptide capable of specifically binding IgM antibodies to human cytomegalovirus, preferably the peptides A1C2 and F3.

A kit suitable for use in this invention on an automated instrument comprises:

(a) microparticles coated with at least a portion of human cytomegalovirus, preferably pp150, more preferably purified recombinant HCMV antigen, suspended in a diluent containing at least one peptide capable of specifically binding IgM antibodies to human cytomegalovirus, preferably the peptides A1C2 and F3;

(b) IgM conjugate in a diluent; and (c) buffered diluent containing a blocking agent.

It is preferred that the diluent in (a) be a buffered sucrose/calf serum diluent. It is preferred that the conjugate in (b) be goat anti-human IgM alkaline phosphatase conjugate and the diluent in (b) be a buffered calf serum. It is preferred that the blocking agent in (c) be calf serum.

A kit suitable for use in another embodiment of this invention comprises:

(a) a strip of material, preferably a strip made of nitrocellulose, containing HCMV antigens, preferably purified viral and recombinant HCMV antigens;

(b) sample dilution buffer containing at least one peptide capable of specifically binding IgM antibodies to human cytomegalovirus, preferably the peptides A1C2 and F3;

(c) IgM conjugate in a diluent, preferably goat anti-human IgM alkaline phosphatase conjugate in a buffered calf serum diluent;

(d) buffered wash solution; and (e) color development reagent.

In the method, the reagent, and the kit, the amount of the at least one peptide capable of specifically binding IgM antibodies to human cytomegalovirus must be sufficient to bind low levels of human cytomegalovirus-specific IgM antibody present in patient specimens not indicative of acute or recent human cytomegalovirus infection, yet, not so great that the at least one peptide capable of specifically binding IgM antibodies to human cytomegalovirus binds medium to high levels of human cytomegalovirus-specific IgM antibody present in patient specimens indicative of acute or recent human cytomegalovirus infection.

This invention improves the performance of a diagnostic immunoassay for the detection of herpesvirus-specific IgM antibody in patient specimens. The improved performance includes, but is not limited to, high diagnostic assay specificity combined with high diagnostic assay sensitivity, low false positive and false negative results, improved detection of herpesvirus-specific IgM antibody indicative of acute and recent infection, improved non-detection of herpesvirus-specific IgM antibody not indicative of an acute and recent infection, and good correlation with a virological diagnosis as determined by virus isolation, antigenemia, or PCR. In the case of human cytomegalovirus, a recent infection is one that has occurred within the previous eight months.

BRIEF DESCRIPTION OF THE DRAWINGS

FIGS. 3 and 4 are schematic representations of the construction of plasmids pMB28: lacZ-A1C2 and pMB34:lacZ-A1C2F3;

FIGS. 6 and 7 show two tables comparing experimental data relating to the detection of IgG and IgM from HCMV-infected subjects, by ELISA assay, using the entire virus or different recombinant fusion proteins, including one according to a first aspect of the invention of U.S. Ser. No. 08/765,856;

FIGS. 14B, C, D show respectively: the nucleotide sequence of the plasmid pJO200, including the intended modification site at plasmid residues 151 to 180 (5'-3'); the double-stranded structure of the mutagenic oligonucleotide, 5'CGCGACGT3', synthesized for ligation into plasmid pJO200/MluI/CIAP; and the nucleotide sequence of the plasmid pJO200,MluI, including the modified residues 151 to 180 (5'-3');

DETAILED DESCRIPTION

Figure 1:
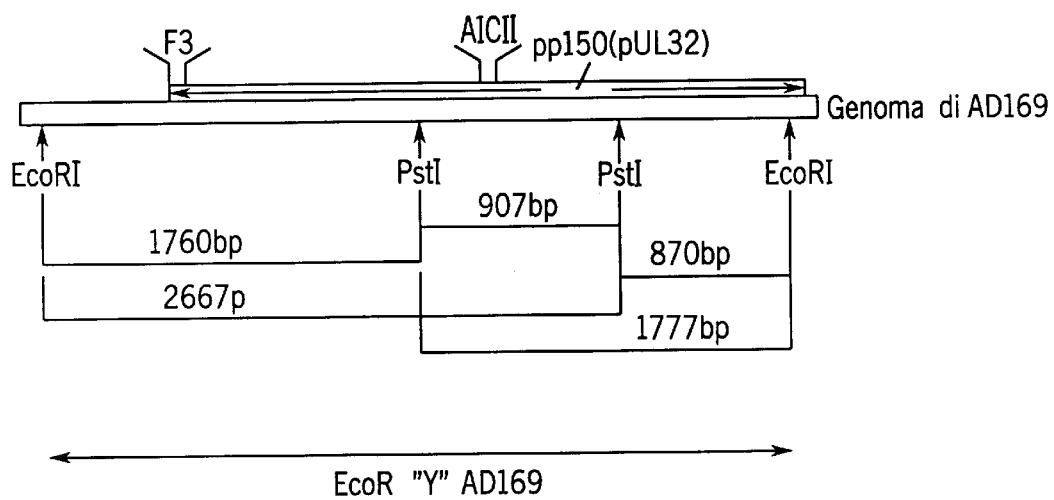
FIG. 1 illustrates schematically the position of the DNA fragments encoding two of the portions characterizing one of the fusion proteins according to the invention of U.S. Ser. No. 08/765,856, in gene UL32 contained in EcoRI-Y fragment of the virus strain AD169.

As used herein, the expression "herpesvirus" means the group of human herpesviruses including herpes simplex virus types 1 and 2, varicella-zoster virus, cytomegalovirus, Epstein-Barr virus, and human herpesvirus types 6, 7, and 8. These large enveloped DNA viruses are responsible for a broad spectrum of clinical illness and share the unique characteristic of becoming latent in the body after a primary infection and having the potential for subsequent reactivation after varying periods of time. Herpesvirus is described in greater detail in *Zinsser Microbiology*, edited by Joklik, Willett, and Amos, Eighteenth Edition, Appleton-CenturyCrofts (1984:Norwalk, Conn.), pp. 997–1012, incorporated herein by reference.

As used herein, the expression "low risk" refers to an individual who has not had a recent HCMV infection. By "recent" is meant within the previous 0 to 13 months.

The expression "solid phase", as used herein, refers to any material to which analyte, analyte complexes, or assay reagents become bound and from which unreacted assay reagents, test sample, or test solutions can be separated. The solid phase generally has a specific binding member attached to its surface to form a "solid phase reagent", that allows the attachment of the analyte or another assay reagent. Specific binding members that are attached to the solid phase may be selected to directly bind the analyte or to indirectly bind the analyte by means of an ancillary specific binding member, which can be attached to the solid phase reagent before, during, or after contacting the solid phase reagent with the test sample and/or other assay reagents.

It will be understood, of course, that the solid phase may comprise multiple components and that the immobilized specific binding member can be bound directly to any or all components of the solid phase. For example, a multiple component solid phase can include a solid phase reagent that is physically entrapped or retained and immobilized within a second or supplementary component of the solid phase by a physical, chemical, or biochemical means. As a further example, an analyte-specific binding member can be attached to insoluble microparticles, which are subsequently retained by a porous material. By "retained" it is meant that the microparticles, once on the porous material, are not capable of substantial movement to positions elsewhere within the porous material. A first solid phase component, which itself can be a solid phase reagent, can be retained by a supplementary component of the solid phase before, during, or after contacting the first solid phase component with the test sample and/or other assay reagents. In most embodiments, however, the specific binding member is bound or attached to a single solid phase component prior to contacting the thus formed mobile solid phase reagent with the test sample or other assay reagents.

The specific binding member may be bound to the solid phase by physical means, such as, for example, by passive, non-covalent attachment of the specific binding member to the solid phase, or chemical means, such as, for example, by means of a covalent bond. The specific binding member should be bound to the solid phase in such a way that substantially none of the specific binding members detach during the subsequent reactions and wash steps. Regardless of the specific binding member and the coupling method selected, the specific binding member must be able to bind to antibody after being coupled to the solid phase.

A solid phase according to the present invention may be a mixture of microparticles with binding members specific for antibody chemically or physically bound to the microparticles. Microparticles that can be used in this invention are preferably made of polymeric material, and more preferably include microparticles derived from polymers having styrene units or polymers having acrylate units. The microparticles are preferably substantially spherical and preferably have radii ranging from about 0.1 μm to about 0.25 inches. A preferred method for separating these particles from the test sample involves capture of the microparticle on a porous matrix, such as a glass fiber.

Other solid phases that can be used include a mixture of magnetizable microparticles having binding members specific for antibody chemically or physically bound to the microparticles. Magnetizable microparticles that are useful in this invention preferably have ferric oxide or chromium oxide cores and a polymeric coating. Such coatings are preferably made from homopolymers and copolymers having styrene units, homopolymers and copolymers having carboxylated styrene units, or homopolymers and copolymers having acrylate or methacrylate units.

Other solid phases that are known to those skilled in the art include the walls of wells of reaction trays, wells of microtiter trays, tubes, polymeric beads, nitrocellulose strips, membranes, and the like. Natural, synthetic, and naturally occurring materials that are synthetically modified can be used as the material of the solid phase. Such materials include polysaccharides, e.g., cellulosic materials, such as, for example, paper and cellulosic derivatives, such as cellulose acetate and nitrocellulose; silica; inorganic materials, such as, for example, deactivated alumina, diatomaceous earth, $MgSO_4$, or other inorganic finely divided material uniformly dispersed in a porous polymeric matrix, wherein the matrix may comprise one or more polymers such as homopolymers and copolymers of vinyl chloride, e.g., polyvinyl chloride, vinyl chloride-propylene copolymer, and vinyl chloride-vinyl acetate copolymer; cloth, both naturally occurring (e.g., cotton) and synthetic (e.g., nylon); porous gels, such as silica gel, agarose, dextran, and gelatin; polymeric films, such as polyacrylamide; and the like. In any case, the solid phase should have sufficient strength to maintain the desired physical shape and should not interfere with the production of a detectable signal. Strength can be provided by means of a support.

As used herein, the term "peptide" means a natural or synthetic compound containing two or more amino acids linked by the carboxyl group of one amino acid and the amino group of another. Peptides suitable for use in this invention can be prepared by chemical synthesis and by recombinant techniques.

As used herein the term "conjugate" means an entity comprising two or more species of molecule covalently bonded to form a hybrid molecule, such as, for example, an antibody bound to a label group. The expression "label" means a group attached to an antibody or an analyte or an analyte analogue to render the reaction between the antibody and the analyte or analyte analogue detectable. Representative examples of labels include enzymes, radioactive labels, fluorescein, and chemicals that produce light. A label is any substance that can be attached to an antibody or a derivative of an antibody and that is capable of producing a signal that is detectable by visual or instrumental means. Various labels suitable for use in this invention include catalysts, enzymes, liposomes, and other vesicles containing signal producing substances such as chromogens, catalysts, fluorescent compounds, chemiluminescent compounds, enzymes, and the like. A number of enzymes suitable for use as labels are disclosed in U.S. Pat. No. 4,275,149, incorporated herein by reference. Such enzymes include glucosidases, galactosidases, phosphatases and peroxidases, such as alkaline phosphatase and horseradish peroxidase, which are used in conjunction with enzyme substrates, such as fluorescein di(galactopyranoside), nitro blue tetrazolium, 3,5',5,5'-tetranitrobenzidine, 4-methoxy-1-naphthol, 4-chloro-1-naphthol, 4-methyl-umbelliferyl phosphate, 5-bromo-4-chloro-3-indolyl phosphate, chemiluminescent enzyme substrates, such as the dioxetanes described in WO 88100694 and EP 0-254-051-A2, and derivatives and analogues thereof. Preferably, the label is an enzyme and most preferably the enzyme is alkaline phosphatase.

As used herein, when named proteins or peptides, e.g., H10, A1C2, F3, in a fusion protein are separated by a virgule, i.e., "/", it is intended that the named proteins can occur in any order in that fusion protein. When named proteins or peptides, e.g., H10, A1C2, F3, in a fusion protein are separated by a hyphen, i.e., "-", it is intended that the named proteins must occur in the order recited in that fusion protein.

The present invention relate to all species of herpesvirus. In order to simplify the discussion of the invention, human cytomegalovirus (HCMV) will be discussed in detail. However, it should be noted that the principles discussed in relation to human cytomegalovirus relate to all other species of herpesvirus.

The phosphorylated structural protein of 150Kd, also known as pp150, is;

a constituent of HCMV. The protein pp150 consists of 1048 amino acids encoded by UL32 gene and comprises several immunogenic regions shown to be reactive to IgM and IgG antibodies present in specimens derived from patients with HCMV disease. Immunogenic regions of pp150 are obtainable from virally infected cells, from viral lysates obtained from infected cells, and from purified virions. immunogenic regions of pp150 are also obtainable by chemical synthesis of peptides derived from the pp150 amino acid sequence or by the expression of the UL32 gene, or portions thereof, fused to an expression partner (fusion protein) or not, using an expression system in a suitable prokaryotic or eukaryotic host. The immunogenic regions of pp150 derived from the UL32 gene can be purified from the host organism. Immunogenic regions of pp150 obtainable in these ways can be used as immunological reagents associated with a solid phase for the detection of antibodies in HCMV-infected individuals.

The purpose of the peptides A1C2 and F3 are to bind low levels of pp150 HCMV-specific IgM antibody not indicative of acute or recent infection and therefore prevent their binding to the solid phase and their subsequent detection in a HCMV IgM immunoassay.

Peptides suitable for use in this invention include A1C2 and F3. The peptide A1C2 has the following amino acid sequence, SEQ ID NO 5:

(595–614aa of pp150):

TPTPVNPSTAPAPAPTPTFA

The peptide F3 has the following amino acid sequence, SEQ ID NO 6:

(1006–1048aa of pp150):

GSSPQKSGTGPQPGSAGMGGAKTPS-DAVQNILQKIEKIKNTEE

The peptides A1C2 and F3 can be prepared by synthetic means using a commercially available automated peptide synthesizer. Such preparation is known to one of ordinary skill in the art. Alternatively, the peptides A1C2 and F3 can be prepared by recombinant means as described in U.S. Ser. No. 08/765,856, incorporated herein by reference. Briefly, the gene encoding the A1C2 and F3 amino acid sequences is cloned in an expression vector suitable for expression of this gene in the host organism. The protein is then purified from the host organism using techniques known to one of ordinary skill in the art.

The optimum amount of peptides preferred for use in this invention must be determined for each assay. In general the amounts of peptides must be sufficient to bind low levels of pp150 HCMV-specific IgM antibody present in patient specimens not indicative of acute or recent HCMV infection. However, the amounts of peptides must not be so great that they bind medium to high levels of pp150 HCMV-specific IgM antibody present in patient specimens indicative of acute or recent HCMV infection. The ratio of peptides to fusion protein preferably ranges from about 0.3:1 to about 3:1, based on weight. The ratio of A1C2 to F3 preferably ranges from about 1:2 to about 2:1, based on weight.

The peptides are typically furnished in the form of a powder. Peptides suitable for use in the present invention are commercially available and can be obtained from AnaSpec, Inc., San Jose, Calif. The peptides are dissolved in water prior to use or formation of a reagent.

Other ingredients needed to carry out the assay of this invention include at least one blocking agent. The purpose of the blocking agent is to reduce non-specific binding of immunoglobins to the solid phase. A preferred blocking agent for this invention is calf serum. Calf serum is commercially available from several sources, such as, for example, GIBCO.

A typical HCMV reagent suitable for use in an automated assay is described hereinafter in Comparative Example A.

In order to prepare the reagent suitable for use in the present invention, the A1C2 and F3 peptides are dissolved in water. The dissolved peptides are then added to the reagent described in Comparative Example A to give a final concentration of from about 1 μg/ml to about 10 μg/ml, preferably about 6 μg/ml, of each added peptide in the HCMV reagent. Of course, the concentrations of ingredients can be varied to optimize the composition for different assay formats.

Other reagents needed for the automated analysis for HCMV include the following:

(1) a conjugate, preferably goat anti-human IgM alkaline phosphatase conjugate (Traut's sulfo-SMCC crosslinking agent for crosslinking the enzyme to the immunoglobin) in a buffered calf serum diluent (2) a diluent, preferably a buffered calf serum diluent.

A HCMV IgM low-positive serum (i.e., Index Calibrator) is used for calculation of patient result (Index Value). A bottle of a HCMV IgM positive serum and a bottle of a HCMV IgM negative serum are used as controls. The Index Calibrator is used to calibrate the instrument prior to calculating the sample result, i.e., the index value for the sample. All samples are read by the instrument and expressed as a rate count, which is proportional to the amount of HCMV IgM antibody present in the sample. The Index Value for a patient sample can be calculated as follows:

Index Value=rate counts of patient sample/rate counts of index calibrator

Typical cut-off values are as follows:

0–0.399 Index Value=Negative for HCMV IgM antibody 0.4–0.499 Index Value=Equivocal for HCMV IgM antibody 0.5 or greater Index Value =Positive for HCMV IgM antibody The cut-off value can be modified depending upon the particular circumstances of the assay, to optimize assay sensitivity and specificity.

An automated assay suitable for detecting herpesvirus, such as, for example, HCMV, is described in U.S. Pat. No. 5,358,691, incorporated herein by reference. The assay for herpesvirus, e.g., HCMV, IgM antibody is based on automated random access Microparticle Enzyme Immunoassay Technology. The reagents required for the assay, including microparticles, conjugate, assay diluent, are contained in a reagent pack. All other assay components, including the reaction vessels, matrix cells, line diluent, Microparticle Enzyme Immunoassay (MEIA) buffer, and 4-methylumbelliferyl phosphate (MUP), reside on the instrument. The assay is typically conducted as follows:

(1) The pipetting probe in the kitting center delivers the sample and line diluent (approximately 0.07 ml) to the sample well of the reaction vessel.

(2) The probe then kits the appropriate volumes of assay diluent (approximately 0.25 ml) and conjugate (approximately 0.085 ml) required for the assay from the reagent pack into the designated wells of the reaction vessel.

(3) The probe then delivers the herpesvirus antigen coated microparticles (approximately 0.09 ml) from the reagent pack and an aliquot of the diluted sample (approximately 0.06 ml) to the designated well of the reaction vessel.

(4) The reaction vessel is then transferred to the process carousel. herpesvirus-specific antibodies bind to the microparticles coated with herpesvirus antigen, thereby forming an antigen-antibody complex.

(5) An aliquot of assay diluent (approximately 0.05 ml) is transferred to the glass fiber matrix in the auxiliary carousel. Another aliquot of assay diluent (approximately 0.1 ml) is added to the reaction mixture. The reaction mixture (approximately 0.12 ml) is then transferred to the glass fiber matrix. The microparticles bind irreversibly to the matrix.

(6) The matrix is washed with MEIA buffer to remove antibodies that are not specifically bound to the coated herpesvirus antigens on the microparticles of the solid phase. An aliquot of assay diluent (approximately 0.05 ml) is then transferred to the matrix.

(7) The goat anti-human IgM ($\mu$-chain specific) antibody/alkaline phosphate conjugate is added to the matrix. This conjugate binds to the IgM antibodies bound to the recombinant herpesvirus antigens on the microparticles.

(8) The matrix is then washed with MEIA buffer to remove any unbound enzyme-antibody conjugate.

(9) The enzyme substrate, 4-methylumbelliferyl phosphate (MUP), is added to the matrix. Alkaline phosphatase enzyme present on the matrix attached to goat anti-human IgM catalyzes the hydrolysis of the phosphoryl moiety from MUP, producing a highly fluorescent product which is measured by the optical system of the instrument. The signal intensity is proportional to the amount of herpesvirus-specific IgM antibodies present in the patient sample.

PREPARATION OF REAGENTS FOR DETECTION OF HCMV BY MEANS OF AN AUTOMATED IMMUNOASSAY

The following description of the preparation of reagents suitable for an assay for the detection of HCMV was previously described in U.S. Ser. No. 08/765,856, the entirety of which is incorporated herein by reference.

REAGENT, ENZYMES AND CULTURE MEDIUM

Restriction enzymes, T4 DNA ligase, Calf Intestinal Alkaline Phosphatase (CIAP), polynucleotide kinase, and the Klenow fragment of DNA Polymerase I were purchased from New England Biolabs, Inc., Beverly, Mass. or from Boehringer Mannheim Corp., Indianapolis, Ind. DNA and Protein molecular weight standards, Dalichi pre-cast gradient polyacrylamide gels, and Semi-Dry Blotting System with buffers were obtained from Integrated Separation Systems, Inc., Natick, Mass. Isopropyl-$\beta$-D-thiogalactoside (IPTG), acrylamide, N-N'-methylene-bis-acrylamide, N,N,N',N'-tetramethylethylenediamine (TEMED), 4-chloro-1-napththol, and sodium dodecylsulfate (SDS) were purchased from BioRad Laboratories, Richmond, Calif. Horseradish peroxidase (HRPO)- labeled antibodies were purchased from Kirkegeard & Perry Laboratories Inc., Gaithersburg, Md. "EPICUREAN COLI XL-1 Blue" (recA1, endA1, gyrA96, thi-I, hsdR17, supE44, relAl, lac [F'proAB lacI$^q$ ZdM15 Tn10 (Tet$^r$)]) Supercompetent $E.$ $coli$ cells, DNA isolation kit, RNA isolation kit, and ZAP-cDNA Synthesis kit were obtained from Stratagene Cloning Systems Inc., La Jolla, Calif. GeneAmp reagent kit and AmpliTaq DNA Polmerase were purchased from Perkin-Elmer Cetus, Norwalk, Conn. Nucleotide kit for DNA sequencing with Sequenase and 7-deaza-dGTP and Sequenase version 2.0 DNA Polymerase were obtained from U.S. Biochemical Corp., Cleveland, Ohio. PolyA+ mRNA purification kit was purchased from Pharmacia LKB Biotechnology Inc., Piscataway, N.J. Luria Broth plates with ampicillin (LiSamp plates) were purchased from Micro Diagnostics, Inc., Lombard, Ill. "OPTI-MEM" Medium, fetal calf serum, phosphate-buffered saline (PBS), competent $E.$ $coli$ DH5$\alpha$ (F-$\phi$8OdlacZdM15 d(lacZYA-arciF)U169 deor recAl endAl phoA hsdR17 supE44 $\lambda^-$ thi-1 gyrA96 relA1), and "ULTRAPURE" agarose were purchased from GIBCO BRL, Inc., Grand Island, N.Y. Bacto-Tryptone, Bacto-Yeast Extract, and Bacto-Agar were obtained from Difoo Laboratories, Detroit, Mich. "NZY" Broth was purchased from Becton Dickinson Microbiology Systems, Cockeysville, Md. Salmon Sperm DNA, lysozyme, ampicillin, N-lauroyl sarcosine, thimerosal, buffers, casein acid hydrolysate, urea, surfactants, like "TWEEN 20", diethylpyrocarbonate (DEPC), and inorganic salts were purchased from Sigma Chemical Co., St. Louis, Mo. "SUPERBROTH II" contained 11.25 g/L tryptone, 22.5 g/L yeast extract, 11.4 g/L potassium phosphate dibasic, 1.7 g/L potassium phosphate monobasic, 10 ml/L glycerol, adjust pH to 7.2 with sodium hydroxide. Tris-buffered saline (TBS) consisted of 20 mM Tris, 150 mM NaCl, pH 7.5. Tris-buffered saline "TWEEN 20" consisted of TBS+0.05% "TWEEN 20". Membrane blocking solution consisted of 1% Bovine Serum Albumin, 1% Casein acid hydrolysate, 0.05% "TWEEN 20" in TBS. Rubazyme specimen dilution buffer (Rubazyme SDB) consisted of 100 mM Tris, pH 7.5, 135 mM NaCl, 10 mM EDTA, 0.2% "TWEEN 20", 0.01% thimerosal, and 4% bovine calf serum. Rubazyme conjugate diluent dilution buffer consisted of 100 mM Tris, pH 7.5, 135 mM NaCl, 0.01% thimerosal, and 10% bovine calf serum. "HRP" color development solution consisted of 0.06% 4-chloro-1-napththiol, 0.02% H2O2, and 0.2% methanol in TBS. SDS-PAGE loading buffer consisted of 62 mM Tris, pH 6.8, 2% SDS (Sodium Dodecyl Sulphate), 10% glycerol, 5% β-mercaptoethanol, and 0.1% bromophenol blue. TE buffer consisted of 10 mMi Tris, 1 mM EDTA, pH 8.0. Polystyrene microparticles were purchased from Polysciences, Inc., Warrington, Pa.

VIRUS PROPAGATION AND PREPARATION OF cDNA

CMV strain AD169 and Towne were propagated in human fibroblasts grown in "OPTI-MEM" Medium supplemented with 5% fetal calf serum. After 6 days post-infection, the infected cells were harvested by centrifugation, washed with PBS, and homogenized with a glass-PTFE ("TEFLON") homogenizer. Total viral DNA was isolated as described in Mocarski, E. S. et al., Proc.Nat.Acad.Sci 82:1266, 1985. Total RNA was isolated from the homogenized cells using the RNA Isolation Kit (Stratagene Cloning Systems, La Jolla, Calif.) and polyA+ RNA was isolated using a mRNA Isolation Kit (Pharmacia Biotech, Piscataway, N.J.). HCMV cDNA was synthesized from the purified viral mRNA using a "ZAP-cDNA" Synthesis Kit (Stratagene Cloning Systems, La Jolla, Calif.).

GENERAL METHODS

All enzyme digestions of DNA were performed according to suppliers' instructions. At least 5 units of enzyme were used per microgram of DNA, and sufficient incubation time was allowed for complete digestion of DNA. Supplier protocols were followed for the various kits used in manipulation of DNA and RNA, and also for PCR and sequence of DNA. Standard procedures were used for (1) small scale preparation and large scale preparation of plasmid DNA from *E. coli*, (2) preparation of phage lysate DNA from *E. coli* cells infected with phage λ, (3) preparation of phage lysates for the absorption of anti-*E. coli* antibodies, (4) extraction with phenol-chloroform, (5) precipitation of DNA with ethanol, (6) restriction analysis of DNA on agarose gels, (7) purification of DNA fragments from agarose and polyacrylamide gels, (8) filling the recessed 3' termini created by digestion of DNA with restriction enzymes using the Klenow fragment of DNA Polymerase I, (9) ligation of DNA fragments with T4 DNA ligase, and (10) preparation of competent *E.coli* TB1 cells (F- ara d(lac-proAB) rpsL φ80diacZdM15 hsdR17) as described in Sambrook, Fritsch, and Maniatis, Molecular Cloning: A Laboratory Manual, 2nd ed., New York: Cold Spring Harbor Laboratory Press 1989, the content of which is hereby incorporated by reference. The DNA fragments for cloning into plasmids that were generated by PCR amplification were extracted with phenol-chloroform and precipitated with ethanol prior to restriction enzyme digestion of the PCR reaction mixture.

Oligonucleotides for PCR and DNA sequencing were synthesized on an Applied Biosystems Oligonucleotide Synthesizer, model 380B or 394, per manufacturer's protocol.

Construction of lacZ-H10 expression Vector pROSH10 (Preparation A)

Figure 2:
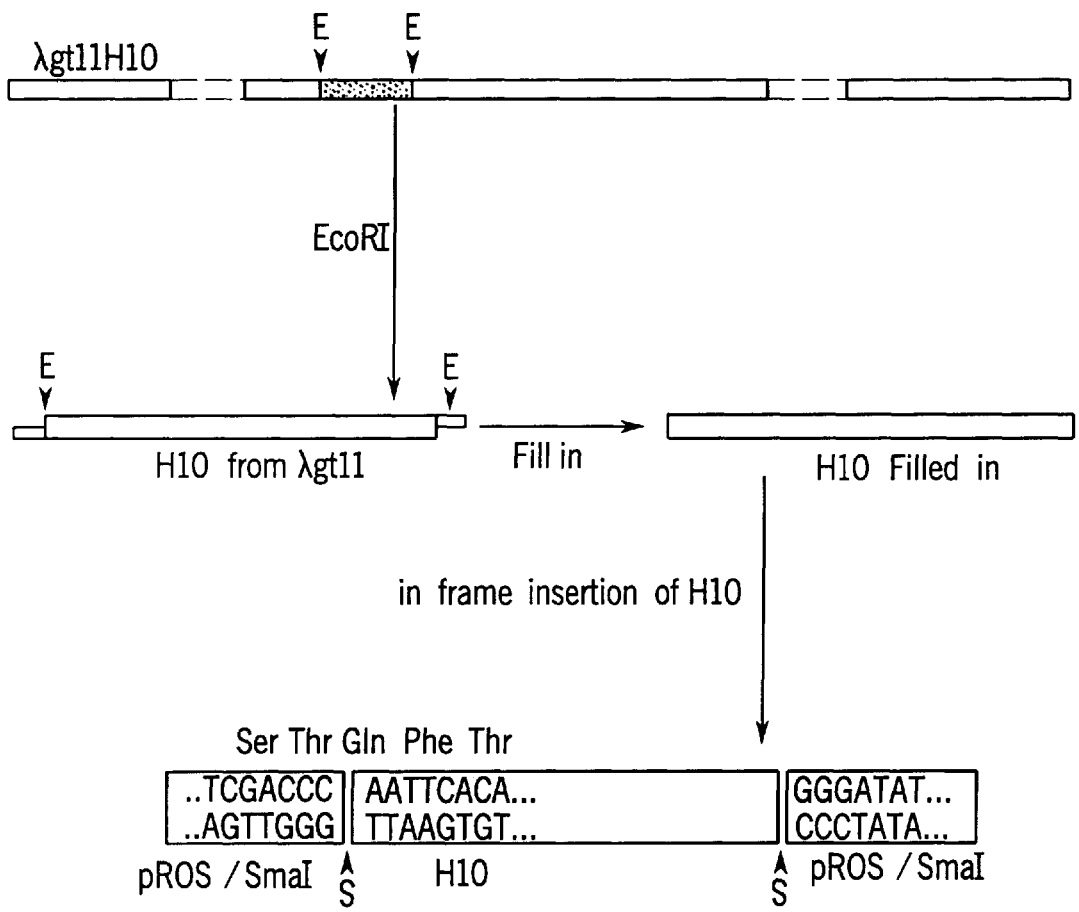

Operating with recombinant DNA standard methods, as described by Maniatis et al., (1982. Molecular cloning: a laboratory manual. Cold Spring Harbor Laboratory. Cold Spring Harbor, N.Y.) and from plasmids pROS supplied by the authors thereof (cf. Ellinger et at.), the genome of a clone, obtained from early gene expressing phage Lambda Gt11, which produces a fusion protein with β-galactosidase, highly reactive with CMV-positive sera, was purified. The genome was then digested with restriction enzyme EcoRI to extract the DNA fragment expressed by the phage. The fragment was then cloned into vector pUC18 and sequenced. The sequence represented a fragment of 699 base pairs expressing 233 aminoacids at COOH terminus of pp52 (UL44). The fragment was then cloned at site SmaI of expression vector pROS, after filling in the EcoRI ends of the fragment, as illustrated schematically in FIG. 2. The plasmid so obtained was named pROSH10.

Construction of lacZ-F3 expression Vector pGT1 (Preparation B)

Operating with the methods described in Preparation A, the genome of aL clone, obtained from early gene expressing phage Lambda Gt11, which produces a fusion protein with β-galactosidase, highly reactive with CMV-positive sera, was purified. The genome was then digested with restriction enzyme EcoRI to extract the DNA fragment expressed by the phage. The fragment was then cloned into vector pUC18 and sequenced. The sequence represented a fragment of 132 base pairs expressing 44 aminoacids at COOH terminus of p150 (UL32). The fragment was then cloned at site SmaI of expression vector pROS, after filling in the EcoRI ends of the fragment, as illustrated schematically in FIG. 2 referred to as Preparation A. The plasmid so obtained was named pGT1.

Construction of lacZ-A1 C2F3 expression Vector pMB34 (Preparation C)

The plasmid pMB34 is a derivative of the lacZ expression vector pROS described in Ellinger et al., J. Clin. Micro. 27: 971, 1989. This vector contains a truncated form of the lacZ gene (1–375 amino acids) with a polylinker cloning site located downstream of the lacZ gene. The pMB34 plasmid was constructed in two steps by joining two regions of ppUL32, which encodes the basic phosphoprotein of 150 kD of HCMV, to the 3' end of the facZ gene in pROS.

A. Construction of pMB28: lacZ-A1 C2

Figure 3:
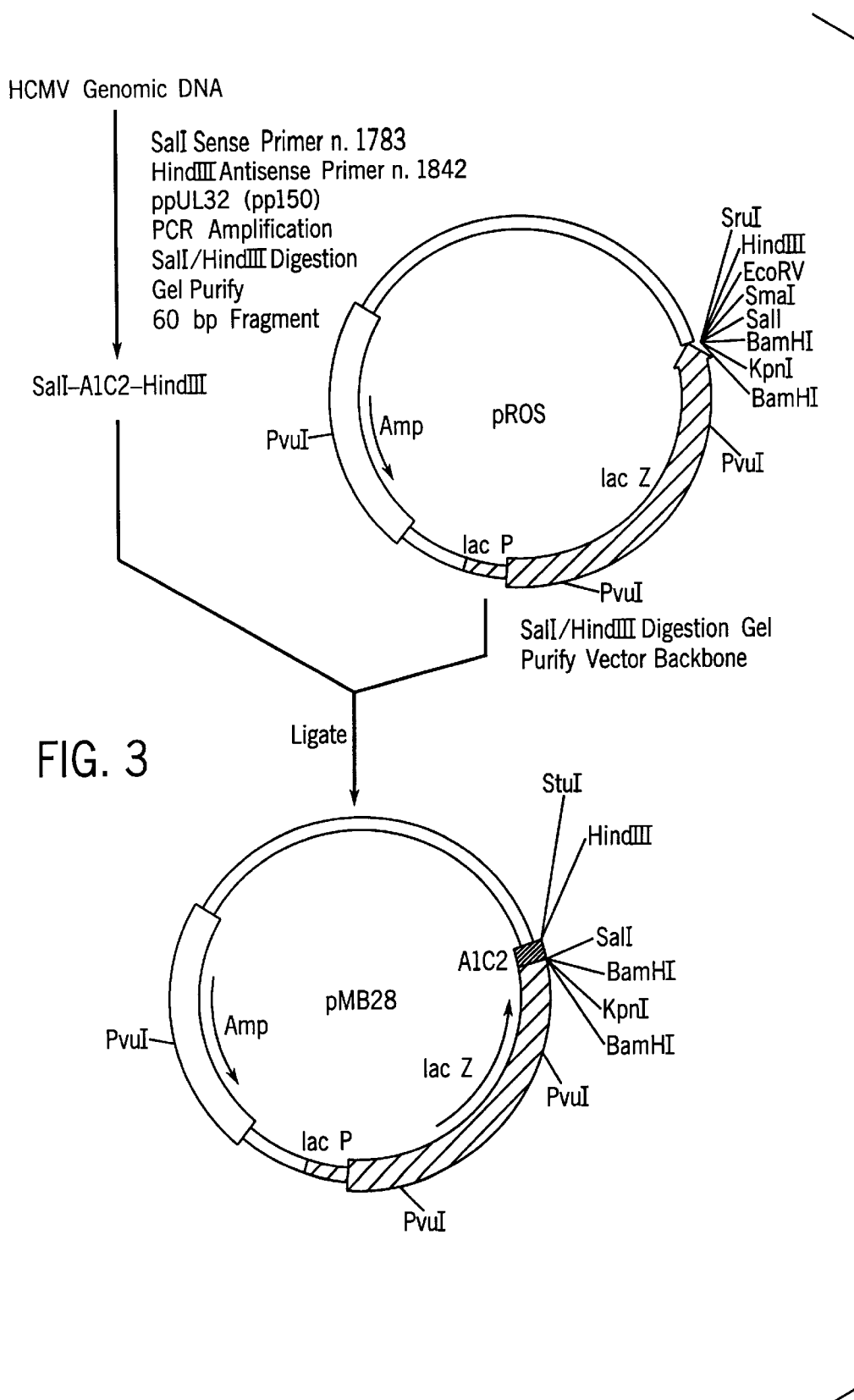

The plasmid pMB28 is a derivative of plasmid pROS as shown in FIG. 3.

This plasmid was constructed by cloning a DNA fragment containing HCMV-A1C2, obtained by PCR amplification of Human Cytomegalovirus (HCMV) genomic DNA from the region of ppUL32 encoding amino acids 595–614 of pp150

(nucleotides 1763–1842), into the polylinker region of pROS. Large scale plasmid DNA (pROS) was isolated from DH5α cells operating as described in general methods. Plasmid pROS was digested with SalI and HindIII and the vector backbone was purified on an agarose gel. A sense primer starting at nucleotide 1783 of ppUL32 containing a SalI site and an antisense primer starting at nucleotide 1842 of ppUL32 containing a HindIII site were synthesized and added to a PCR reaction mixture containing genomic HCMV DNA. After PCR amplification, the reaction mixture was digested with SalI and HindIII, and the 60 base pair fragment containing A1C2 (nucleotides 1733–1842) was purified on an agarose gel. This purified fragment was then ligated to purified pROS/SalI/HindIII overnight at 16° C. The next day the ligation mixture was transformed into competent DH5α cells. Small scale preparation DNA was prepared from the transformants and screened for the presence of the 60 base pair fragment in pROS at the end of the lacZ gene. Plasmid pMB28, which contains the A1C2 fragment, was isolated. The DNA sequence of A1C2 in pMB28 was confirmed and the A1C2 coding region was in frame with the lacZ coding sequence.

B. Construction of pMB34: lacZ-A1 C2F3

The plasmid pMB34 is a derivative of plasmid pMB28, as shown in FIG. 4.

The plasmid pMB34 was constructed by cloning a DNA fragment, containing HCMV-F3 obtained from a λgt11 subclone of ppUL32 encoding amino acids 1006–1043 of ppUL32 (nucleotides 3016–3144) derived from the λgt11 library of Mocarski, E. S. et al. Proc. Nat. Acad. Sci 82: 1266, 1985, into the polylinker region of pMB28 just downstream of the A1C2 DNA sequence. Large scale plasmid DNA (pMB28) was isolated from DH5α cells as described in general methods. Phage lysate DNA was prepared from phage λgt11 clone λ-F3 as described in general methods. Plasmid pMB28 was digested with StuI and the vector backbone with blunt-ends was purified on an agarose gel. Phage λ-F3 DNA was digested with EcoRI and the recessed 3' termini were filled in with the Klenow fragment of DNA Polymerase I, leaving blunt-ends. The blunt-ended 129 base pair λ-F3 fragment was purified on an agarose gel and then blunt-end ligated to pMB28/StuI overnight at 16° C. The next day the ligation mixture was transformed into competent DH5α cells. Small scale preparation DNA was prepared from the transformants and screened for the presence of the 129 base pair fragment in pMB28 at the end of the lacZ gene in the correct orientation. Plasmid pMB34, which contains the F3 fragment in the correct orientation, was isolated. The DNA sequence of F3 in plasmid pMB34 was confirmed and the F3 coding region was in-frame with the lacZ-A1C2 coding sequence. The coding region of the lacZ-A1C2F3 construct in pMB34 contains a bridge of 5 amino acids between A1C2 and F3 as shown below using the International Standard one-letter Codification for amino acids (according to which: L is Leu, Q is Gin, K is Lys, E is Glu, F is Phe):

(1) lacZ(1–375aa)-A1 C2(595–614aa, pp150)-K-L-Q-E-F-F3(1006–1048aa, pp150)

Construction of lacZ-H10A1 C2F3 Expression Vector pMB40 (Preparation D)

Figure 5:
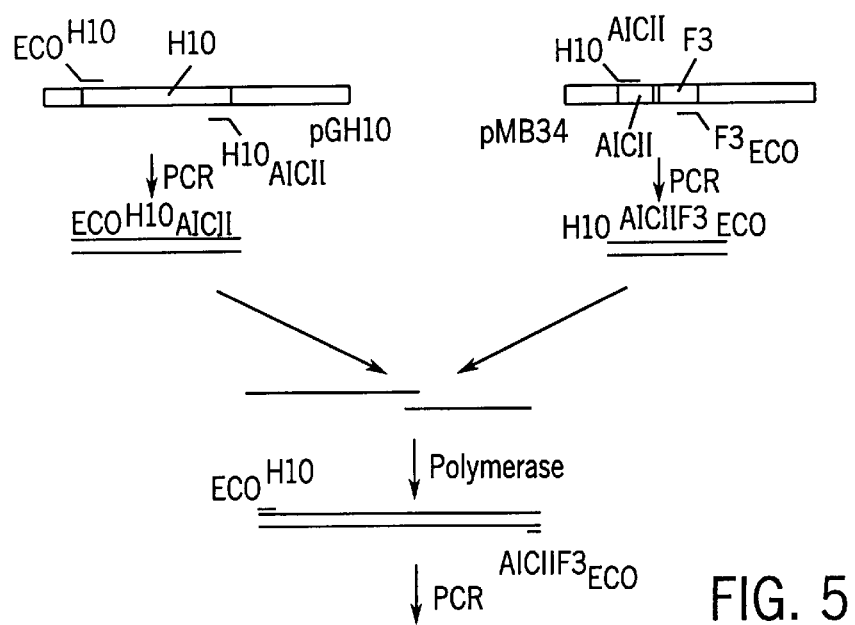
FIGS. 2 and 5 schematically illustrates methods for preparing plasmids used in U.S. Ser. No. 08/765,856.

Starting from the previously described plasmids, and operating with such methods, as have been described in Preparations A, B, and C hereinabove and. as illustrated in FIG. 5, two pairs of oligonucleotides were synthesized, the sequences whereof allow for their use for chain amplification, with PCR, of H10 and A1C2-F3 sequences, respectively, localized in plasmids pROSH10 and pMB34. The oligonucleotide sequences composing said primers are as follows:

$_{Eco}$H10: GAA TTC ACA GCC AAT AAC CGC GTC AGT TTC; (SEQ ID NO: 8)

H10$_{A1C2}$: AGG CGT CGG CGT GCC GCA CTT TTG CTT GGT GTT (SEQ ID NO: 9)

to amplify H10 from pROSH10, introduce a site EcoRI in 5' in the amplified sequence and a sequence of 12 base pairs, homologous of A1C2, in 3' in the amplified fragment; and $_{H10}$A1C2: CM MG TGC GGC ACG CCG ACG CCT GTC MT CCT TCC; (SEQ ID NO: 10)

F3$_{Eco}$: GAA TTC CTA TTC CTC CGT GTT CTT AAT CTT (SEQ ID NO: 11)

to amplify A1C2-F3 fragment from plasmide pMB34, introducing in the amplified product, at 5', a sequence, homologous of H10, and an EcoRI site in 3'. The two fragments, resulting from said two independent amplifications ($_{Eco}$H10$_{A1C2}$ and $_{H10}$A1C2-F3$_{Eco}$) were then mixed, together with external primers $_{Eco}$H10 and F3$_{Eco}$, and subjected to additional amplification. Owing to sequences 3'$_{Eco}$H10$_{A1C2}$ and 5'$_{H10}$A1C2-F3Eco being complementary, the amplified product contains all three epitopes and has an EcoRI site at each end. The amplified sequence was then cloned into pROS and the plasmid derived therefrom, named pMB40, includes, in connection with corresponding site SmaI, DNA sequence SEQ ID No: 1, corresponding to nucleotides 002 to 907.

The plasmids described in Preparations A, B, C, and D hereinabove, were inserted in E. coli, by electroporation and cloned; synthesis of the desired fusion protein was then induced by the addition of IPTG and the proteins so obtained were made competent by lysis of bacterial cells and denaturation of the cell lyses with SDS and β-mercaptoethanol; the proteins were then run in 9%–12% acrylamide gel with SDS-PAGE and then transferred to nitrocellulose, where immunoreactions took place; a preliminary screening of a number of serum samples was carried out by Miniblotter (Immunetics, Cambridge, Mass. USA); both IgG purified ("Endobulin", of lmmuno AG, Wien AT) and a group of IgM-highly positive sera were used at a dilution of 1:100. Individual human serum samples were diluted at 1:80 for IgG and IgM detection; a peroxidase-conjugated anti-g or anti-μ chain was used as a second antibody. Two groups of human serum samples were used: the first group of sera consisted of seventeen HCMV-positive samples, eight whereof with a high IgG titre to HCMV and seven a medium/low level of HCMV-specific IgG, as detected by ELISA; the presence of HCMV-specific IgG was confirmed by immunoblotting. The second group of sera consisted of nineteen HCMV-positive samples, ten whereof with a high IgM titre to HCMV and nine a medium/low level of HCMV-specific IgM, as detected by ELISA; also in this case, the presence of HCMV-specific IgM was confirmed by immunoblotting.

The evaluation of anti-HCMV IgG was carried out with a CMV kit of M.A. Bioproducts (Walkersville, Md. USA); plates were read on a "microELISA" automatic reader (Dynatech Products, Alexandria, Va. USA). To perform linear regression analysis and to standardize the test run, every plate included three serum calibrators. The evaluation of anti-HCMV IgM was carried out with a CMV IgM "ELA" kit of Technogenetics (Hamburg, Germany). The results were interpreted as suggested by the manufacturers.

In order to avoid false positive results, all samples were also subjected to( a test run for the detection of Rheumatoid factor by lattex agglutination (Rheuma-Wellco test of Wellcome, Dartford, Great Britain) and only the negative samples were used for comparison. Results are shown in Tables 1 and 2 of FIGS. 6 (IgG) and 7 (IgM).

As it is clear from the data presented, not only have the results obtained with H10/A1C2/F3 distinctly improved, as compared to those obtained with the other fusion proteins, both to IgG and to IgM, but they are fully superimposable to the results obtained with antigens composed of the entire virus.

Construction of CKS Expression Vector pJQ200

The CKS expression vector pJO200 allows the fusion of recombinant proteins to the CMP-KDO synthetase (CKS) protein. The DNA sequence for the structural gene encoding CKS (the kdsB gene) is published in Goldman et al., J. Biol. Chem. 261:15831, 1986. The amino acid sequence, 248 total, for CKS derived from the DNA sequence, is described in the same article. This pJO200 vector is constructed by a three-step procedure starting with the plasmid pTB201 (FIG. 8) described in Bolling and Mandecki, Biotechniques 8: 468, 1990. The construction plan for plasmid pJO200 involves the removal of two restriction enzyme sites and the addition of a multi-cloning site at the 3' end of the CKS gene. This was done to facilitate the cloning of HCMV (Human Cytomegalovirus) genes encoding protein antigens at the 3' end of CKS. The completed vector contains the coding sequence for 240 amino acids of the original kdsB gene plus an additional 20 amino acids at the end of the CKS gene contributed by the polylinker DNA sequence, for a total of 260 amino acids.

A. Construction of pJO210

The plasmid, pJO210, is a derivative of the CKS expression vector, pTB201. This plasmid was constructed by removing a single EcoRI site present in pTB201 located upstream from the promoter for the CKS gene. Large scale plasmid DNA (pTB201) was isolated from TB1 cells using the techniques described in the section above named "General Methods". The DNA was digested with EcoRI to completion and purified on a polyacrylamide gel. The purified pTB201/EcoRI fragment was then treated with the Kienow fragment of DNA Polymerase I in the presence of deoxynucleotide triphosphates. This enzyme fills in the recessed 3' termini produced after digestion with EcoRI, leaving blunt ends. After treatment with Klenow fragment, the DNA was phenol/chloroform extracted, ethanol precipitated, and resuspended in T4 DNA ligase buffer and ligated at room temperature with T4 DNA ligase for 4 hours. The ligation mixture was transformed into competent TB1 cells. Small scale preparation DNA was prepared from the transformants and screened for the loss of the EcoRI site. Plasmid pJO210, which has lost the EcoRI site, was isolated.

B. Construction of pJO215

Figure 8:
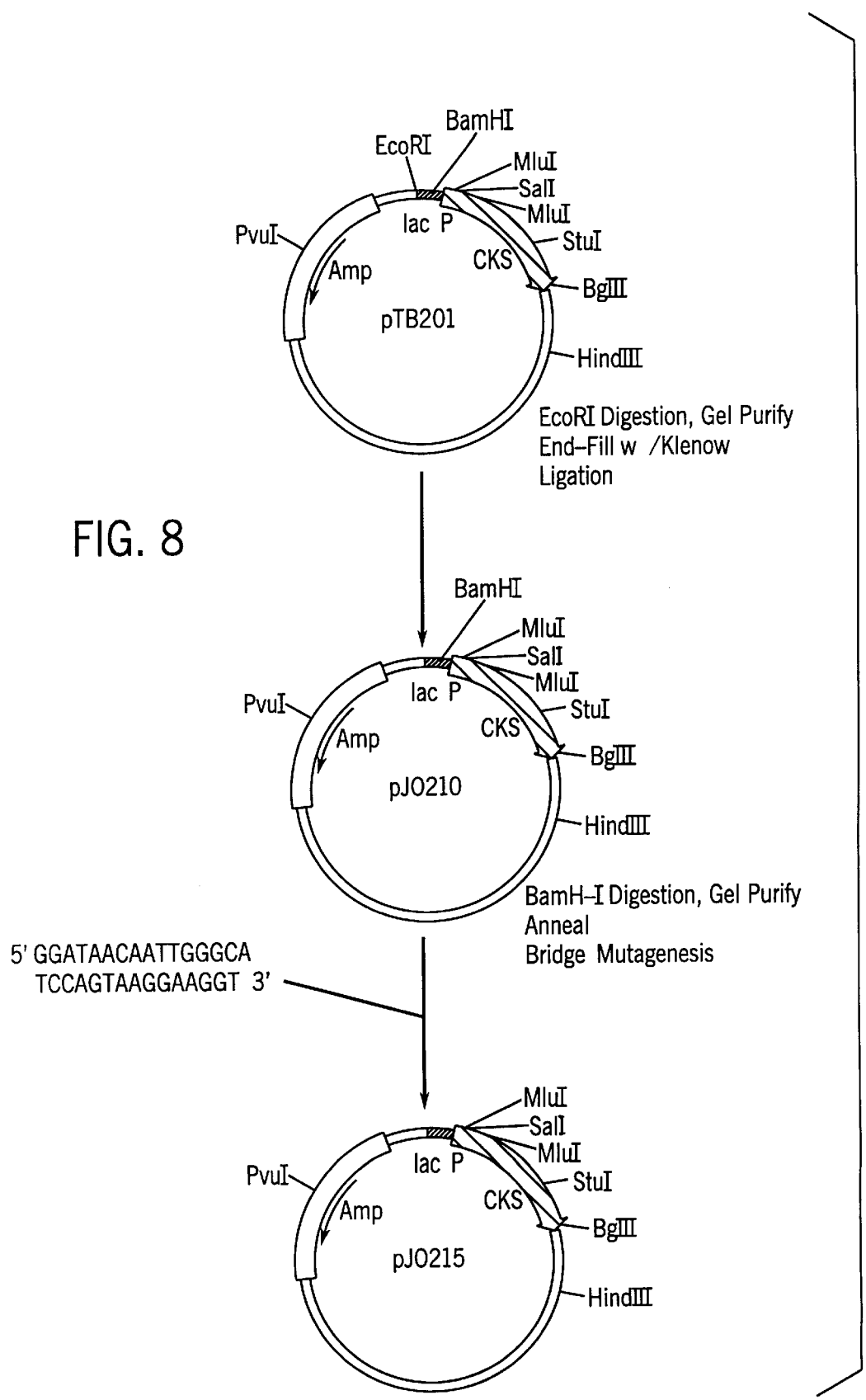
FIG. 8 is a schematic representation of the construction of plasmids pJO210 and pJO215.

The plasmid pJO215 is a derivative of the plasmid pJO210 (FIG. 8). This plasmid was constructed by removing a single BamH-I site located in the promoter for the CKS gene using bridge mutagenesis (Mandecki, W., Proc. Nat. Acad. Sci. 837177,1986). Large scale plasmid DNA (pJO210) was isolated from TB1 cells as described in general methods. The DNA was digested with BamH-I to completion and purified on a acrylamide gel. The purified pJO210/BamH-I fragment was then mixed with the following mutagenic oligonucleotide:

5' GGATAACAAT TGGGCATCCA GTMGGAGGT 3' (SEQ ID NO: 12) (2)

which is complementary to one of the DNA strands of pJO210 in the region of the plasmid spanning the BamH-I site. This oligonucleotide contains a single base change, underlined, which will destroy the BamH-I site when incorporated into plasmid pJO210. After mixing the mutagenic oligonucleotide with pJO210/BamH-I, the mixture was boiled for 3 minutes, cooled to room temperature for 5 minutes and then transformed into competent TB1 cells. Small scale preparation DNA was prepared from the transformants and screened for the loss of the BamH-I site. Plasmid pJO215, which has lost the BamH-I site, was isolated.

C. Construction of pMC200

Figure 9:
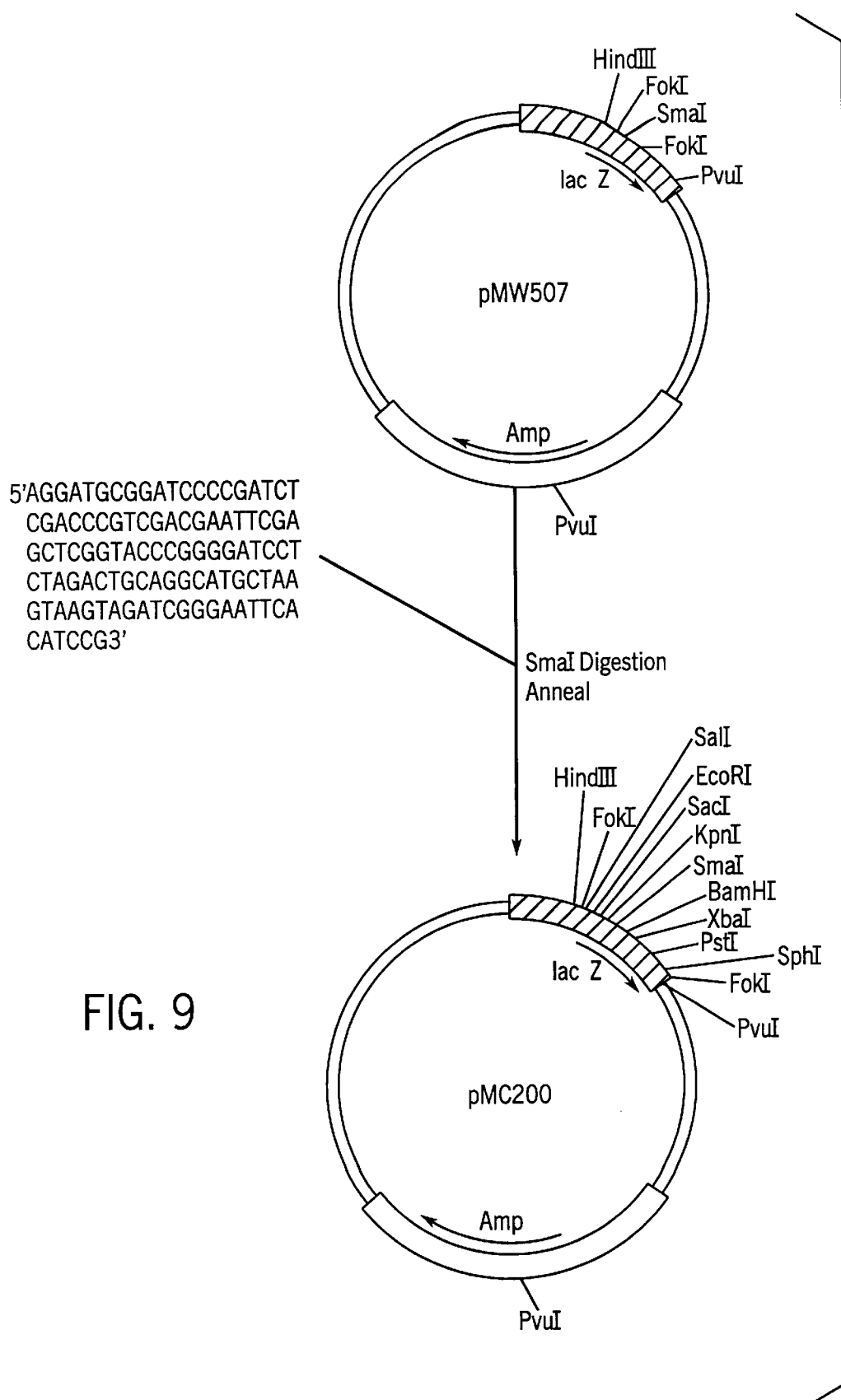
FIG. 9 is a schematic representation of the construction of plasmid pMC200.

The plasmid pMC200 is a derivative of plasmid pMW507 described in Mandecki and Boiling, Gene 68: 101, 1988 (FIG. 9). This plasmid was constructed by cloning a synthetic oligonucleotide containing a multi-cloning site into pMW507 using the FokI method of gene synthesis described by Mandecki and Bolling, 1988. Large scale plasmid DNA (pMW507) was isolatedl from TB1 cells as described in general methods. The DNA was digested to completion with SmaI and then mixed with the following oligonucleotide:

5' AGGATGCGGA TCCCCGATCT CGACCCGTCG ACGAAT-
TCGA (SEQ ID NO: 13) GCTCGGTACC CGGGGATCCT
CTAGACTGCA GGCATGCTAA GTAAGTAGAT CGGGAAT-
TCA CATCCG 3' (3)

which contains FokI arms at the end and several restriction enzyme sites, as follows:

5' FokI arm-BglII sticky end-SalI/AccI/HindII-EcoRI-SstI-KpnI-
SmaI/XmaI-BamH-I-XbaI-PstI-SphI-stop codons -BglII sticky
end-FokI arm 3' (4)

After mixing the oligonucleotide with pMW507/SmaI, the mixture was boiled for 3 minutes, cooled to room temperature for 5 minutes, and then transformed into competent TB1 cells. Small scale preparation DNA was prepared from the transformants and screened for the presence of the multi-cloning site. Plasmid pMC200, which contains the multi-cloning site, was isolated. The DNA sequence of the multi-cloning site was confirmed.

D. Construction of pJO200

Figure 10:
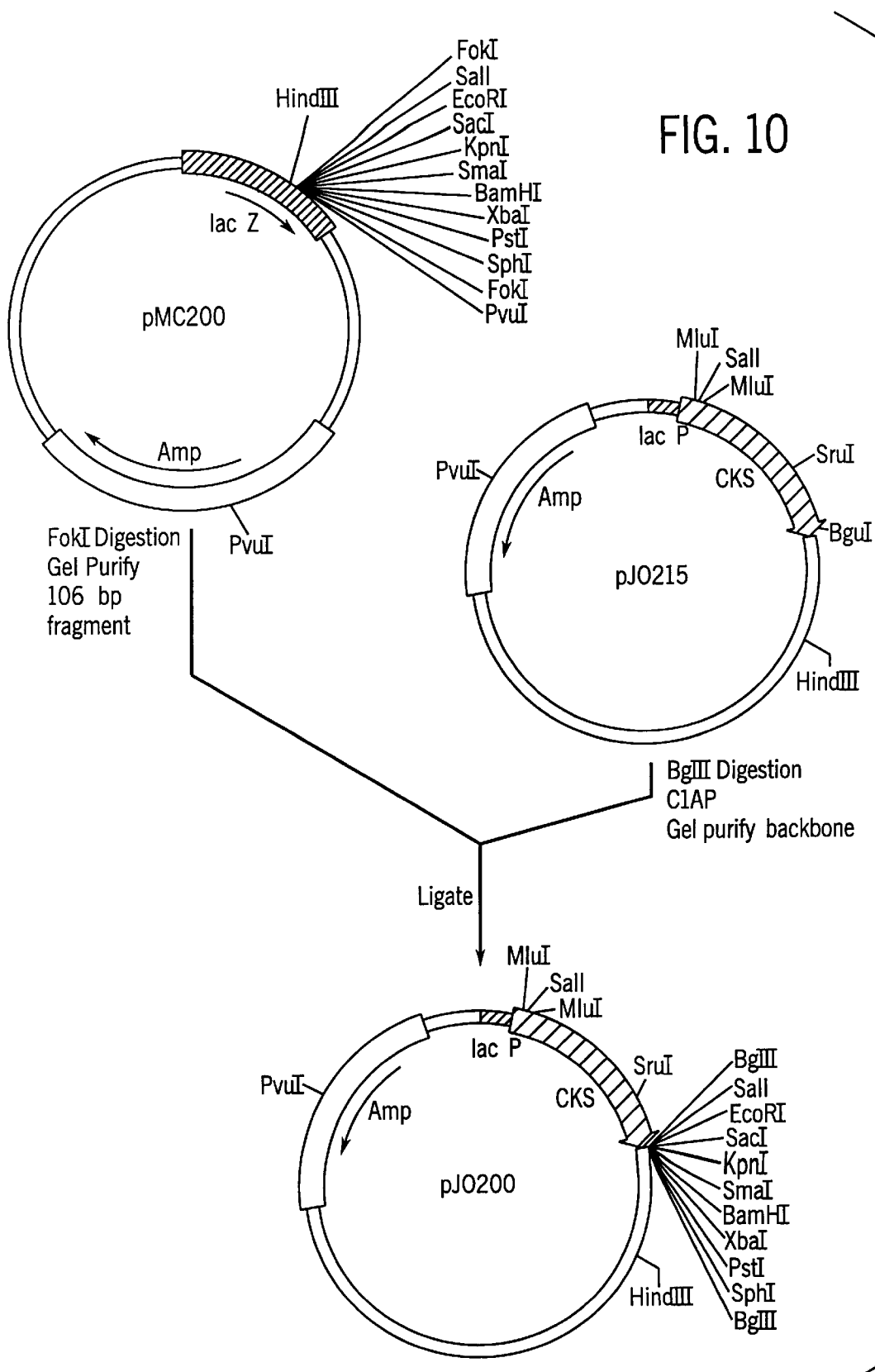
FIG. 10 is a schematic representation of the construction of plasmid pJO200.

The plasmid pJO200 is a derivative of plasmid pJO215 (FIG. 10). This plasmid was constructed by removing the multi-cloning site from pMC200 and cloning this site at the 3' end of the CKS gene in pJO215. Large scale plasmid DNA (pMC200 and pJO215) was isolated from TB1 cells as described in general methods. Plasmid pJO215 was digested to completion with BglII and then treated with calf intestinal alkaline phosphatase (CIAP) to prevent recircularization of the plasmid during the ligation reaction. Plasmid pMC200 was digested with FokI and then the pJO215/BglII/CIAP DNA and the pMC200/FokI DNA containing the multi-cloning site (106 base pairs) were purified on a polyacrylamide gel. Digestion of plasmid pMC200 with FokI releases the multi-cloning site DNA from the plasmid. This DNA contains BglII sticky ends which will readily ligate into pJO215 DNA digested with BglII. These purified DNA fragments were mixed and ligated at 16° C. with T4 DNA ligase overnight. The next day the ligation mixture was transformed into competent TB1 cells. Small scale preparation DNA was prepared from the transformants and screened for the presence of the multi-cloning site in the correct orientation at the BglII site. Plasmid pJO200, which contains the multi-cloning site in the correct orientation, was isolated. The DNA sequence of the multi-cloning site in pJO200 at the BglII site was confirmed.

Construction of lacZ-pp38(106–373aa) Expression Vector pMB38

Figure 11:
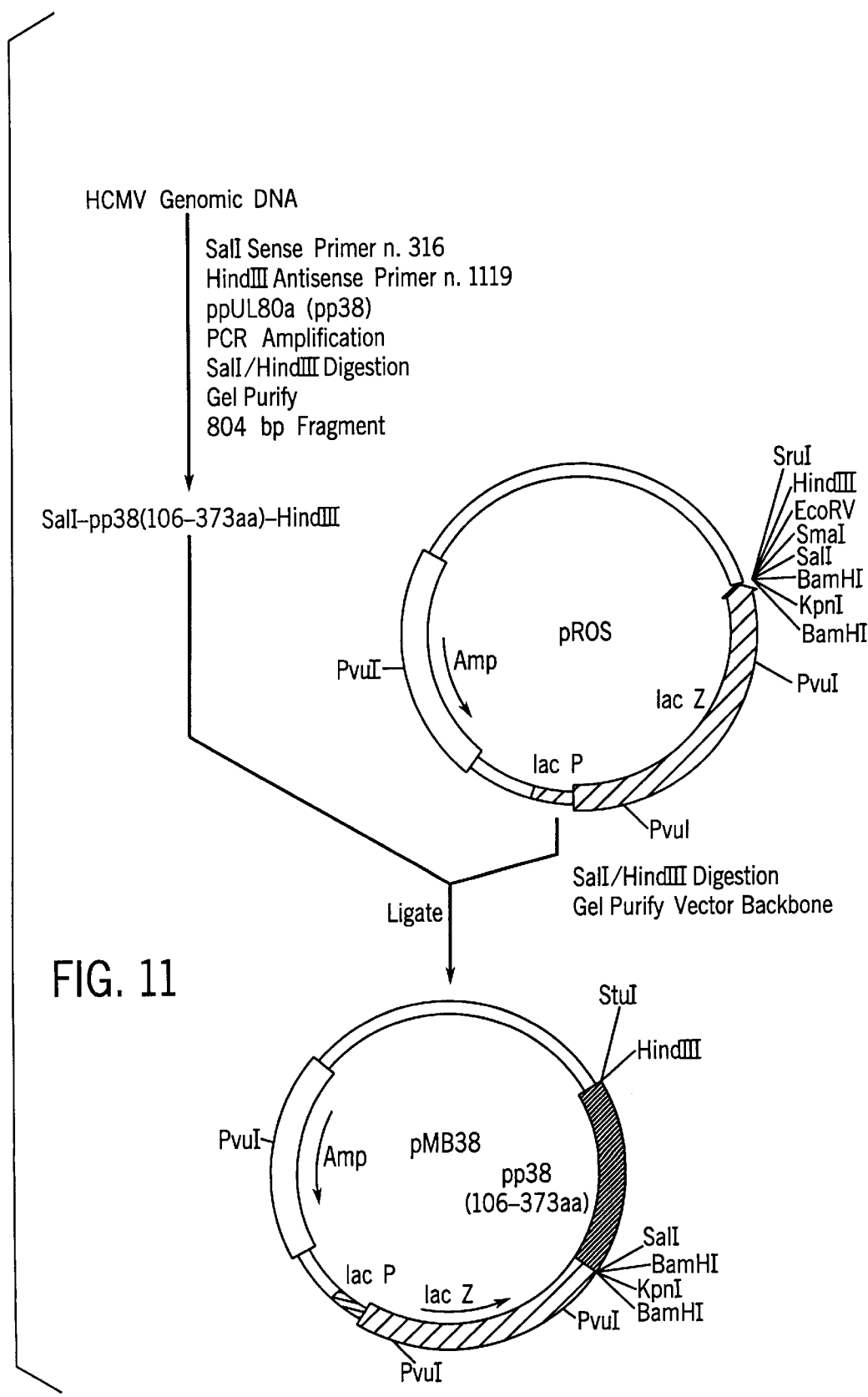
FIG. 11 is a schematic representation of the construction of plasmid pMB38: lacZpp38(106–373aa)

The plasmid pMB38 is a derivative of the lacZ expression vector pROS (FIG. 11). This plasmid was constructed by cloning a DNA fragment containing HCMV-pp38 (106–373aa), obtained by PCR amplification of genomic HCMV DNA from the region of ppUL80a encoding amino acids 106–373aa of pp38 (nucleotides 316–1119), into the polylinker region pROS. The ppUL80a region encodes a phosphoprotein of 38 kD of HCMV. Plasmid pROS was digested with SalI and HindIII and the vector backbone was purified on an agarose gel. A sense primer starting at nucleotide 316 of ppUL80a containing a SalI site and an antisense primer starting at nucleotide 1119 of ppUL80a containing a HindIII site were synthesized and added to a PCR reaction mixture containing genomic HCMV DNA. After PCR amplification, the reaction mixture was digested with SalI and HindIII and the 804 base pair fragment containing pp38(106–373aa) was purified on an agarose gel. This purified fragment was then ligated to purified pROS/ SalI/HindIII overnight at 16° C. The next day the ligation mixture was transformed into competent DH5α cells. Small scale preparation DNA was prepared from the transformants and screened for the presence of the 804 base pair pp38 (106–373aa) fragment in pROS at the end of the lacZ gene. Plasmid pMB38, which contains the pp38(106–373aa) fragment, was isolated. The DNA sequence of pp38 (106–373aa) in pMB38 was confirmed and the pp38 (106–373aa) coding region was in-frame with the lacZ coding sequence.

Construction of CKS-CMV Expression Vectors Based on pJO200 (Preparation E)

The CKS expression vector pJO200 is the building block for a series of five CKS-CMV gene fusion constructs. Two types of CKS-CMV gene fusion plasmids were constructed. One type of CKS-CMV gene fusion plasmid was constructed in which the CMV gene sequence is embedded within the CKS gene at nucleotide 638 of pJO200 (amino acid 171 of CKS) as shown below:

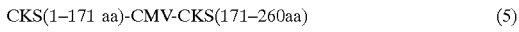
CKS(1–171 aa)-CMV-CKS(171–260aa)    (5)

This method of CKS-CMV gene fusion construction is called epitope-embedding. Fusion proteins expressed in *E. coli* from this type of construct contain the epitopes of the antigen embedded entirely within the CKS amino acid sequence. Plasmid pCMV-1A was constructed in this manner.

Another type of CKS-CMV gene fusion plasmid was constructed in which the CMV gene DNA sequence is linked to the 3' end of the CKS gene at amino acid 248 as shown below:

CKS(1–248aa)-CMV    (6)

Plasmids pCMV-3B, pCMV-4, pCMV-9, and pCMV-26 were constructed in this manner. Large scale plasmid DNA (pJO200) was isolated using general methods for the constructs described below.

A. Construction of pCMV-1A: CKS-A1C2F3-CKS

Figure 12:
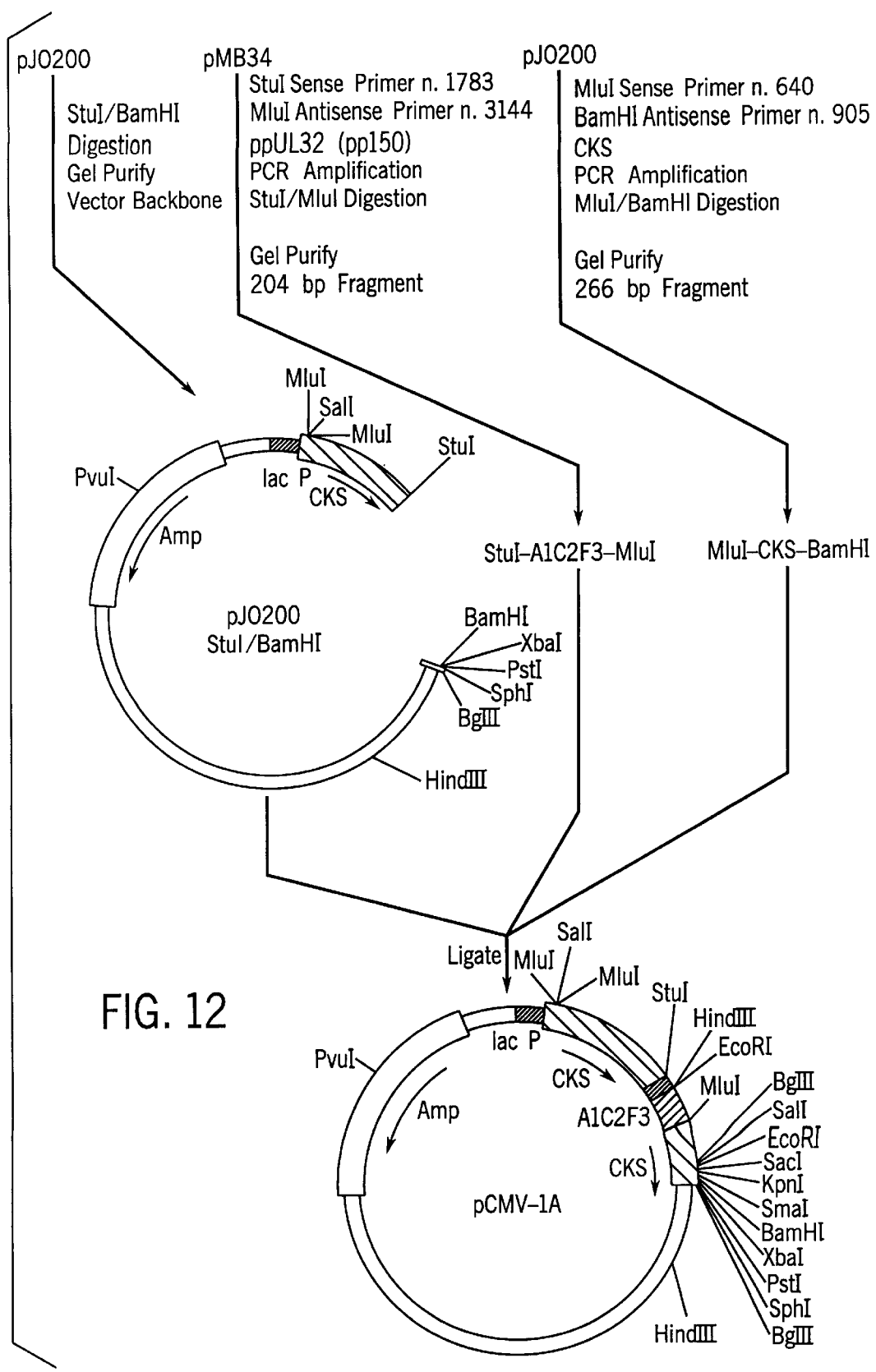
FIG. 12 is a schematic representation of the construction of plasmid pCMV-1A: CKS-A1 C2F3-CKS.

The plasmid pCMV-1A is a derivative of plasmid pJO200 (FIG. 12).

This plasmid was constructed by cloning a DNA fragment containing HCMV-A1C2F3, obtained by PCR amplification of A1C2F3 DNA contained in plasmid pMB34, into the StuI site of pJO200. Large scale plasmid DNA (pMB34) was isolated by general methods. Plasmid pJO200 was digested with StuI and BamH-I and the vector backbone was purified on an agarose gel. This digest removes a portion of the 3' end of the CKS gene which will be restored in the ligation reaction. Into this vector backbone two PCR-derived DNA fragments will be cloned in a three-way ligation reaction. A1C2F3 will be cloned as a StuI/MluI DNA fragment and the remaining 3' portion of the CKS gene will be cloned as a MluI/BamH-I DNA fragment, restoring the complete CKS gene. A sense primer starting at nucleotide 1783 of ppUL32 containing a StuI site and an antisense primer starting at nucleotide 3144 of ppUL32 containing an MluI site were synthesized and added to a PCR reaction mixture containing plasmid pMB34. After PCR amplification, the reaction mixture was digested with StuI and MluI, and the 204 base pair fragment containing A1 C2F3 was purified on an agarose gel. A sense primer starting at nucleotide 640 of pJO200 containing an MluI site and an antisense primer starting at nucleotide 905 of pJO200 containing a BamH-I site were synthesized and added to a PCR reaction mixture containing plasmid pJO200. After PCR amplification, the reaction mixture was digested with MluI and BamH-I, and the 266 base pair fragment containing the 3' portion of the CKS gene was gel purified. These purified PCR-derived DNA fragments were then ligated to pJO200/StuI/BamH-I overnight at 16° C. The next day the ligation mixture was transformed into competent XL-1 Blue cells. Small scale preparation DNA was prepared from the transformants and screened for the presence of A1C2F3 inserted at the StuI site of pJO200.

Plasmid pCMV-1A, which contains A1C2F3 inserted at the StuI site, was isolated. The DNA sequence of A1C2F3 and the 3' end of the CKS gene was confirmed. The coding region of the CKS-A1C2F3-CKS construct in pCMV-1A contains a bridge of 2 amino acids (threonine and arginine) contributed from the MluI site between A1C2F3 and the 3' end of CKS. In addition, amino acid 171 of CKS is duplicated in the construct as shown below:

CKS(1–171 aa)-A1 C2-K-L-Q-E-F-F3-T-R-CKS(171–260aa)    (7)

B. Construction of pCMV-3B: OKS-H10

Figure 13A:
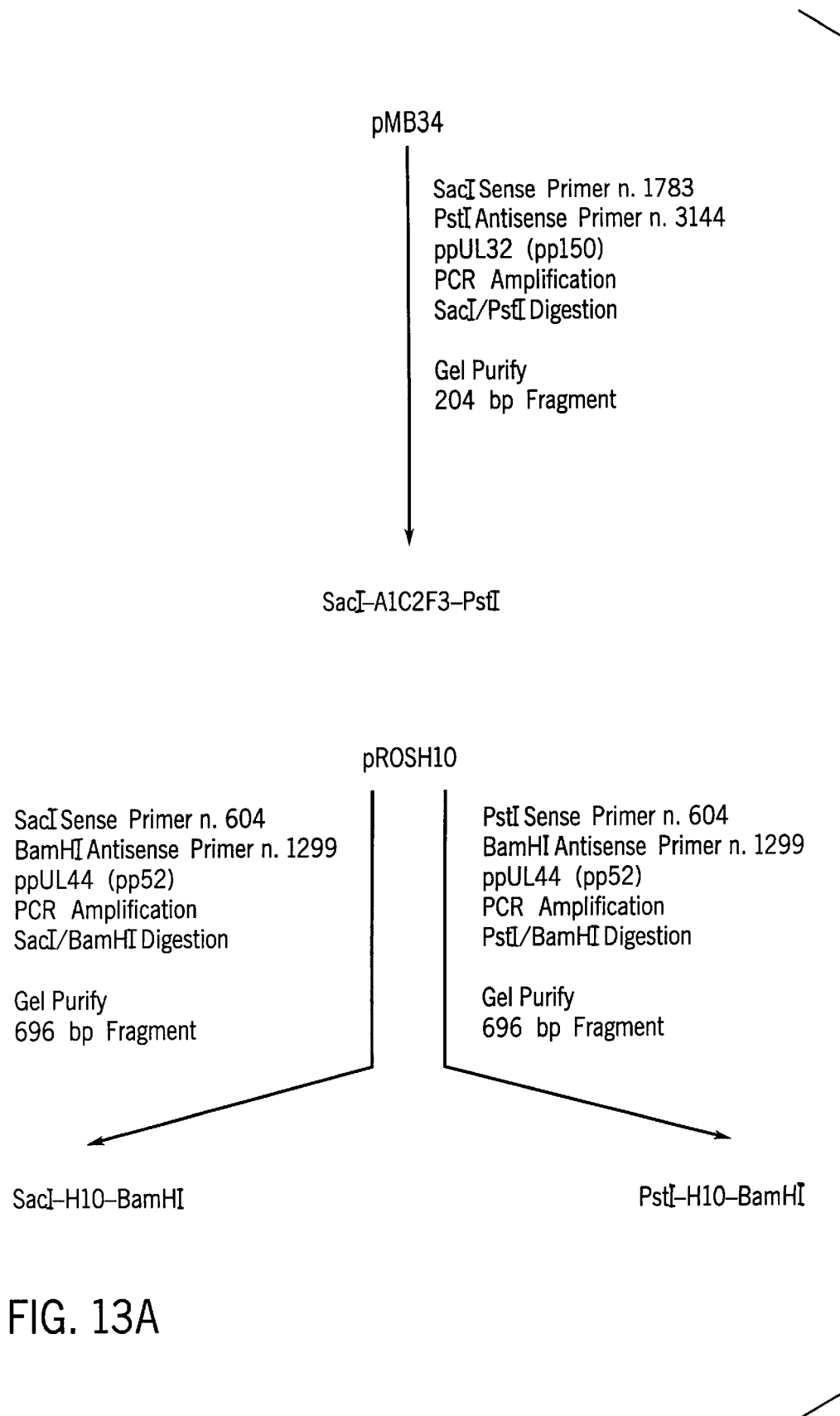
FIG. 13A shows preparation of PCR fragments containing the A1C2F3 and H10 DNA sequences.
Figure 13B:
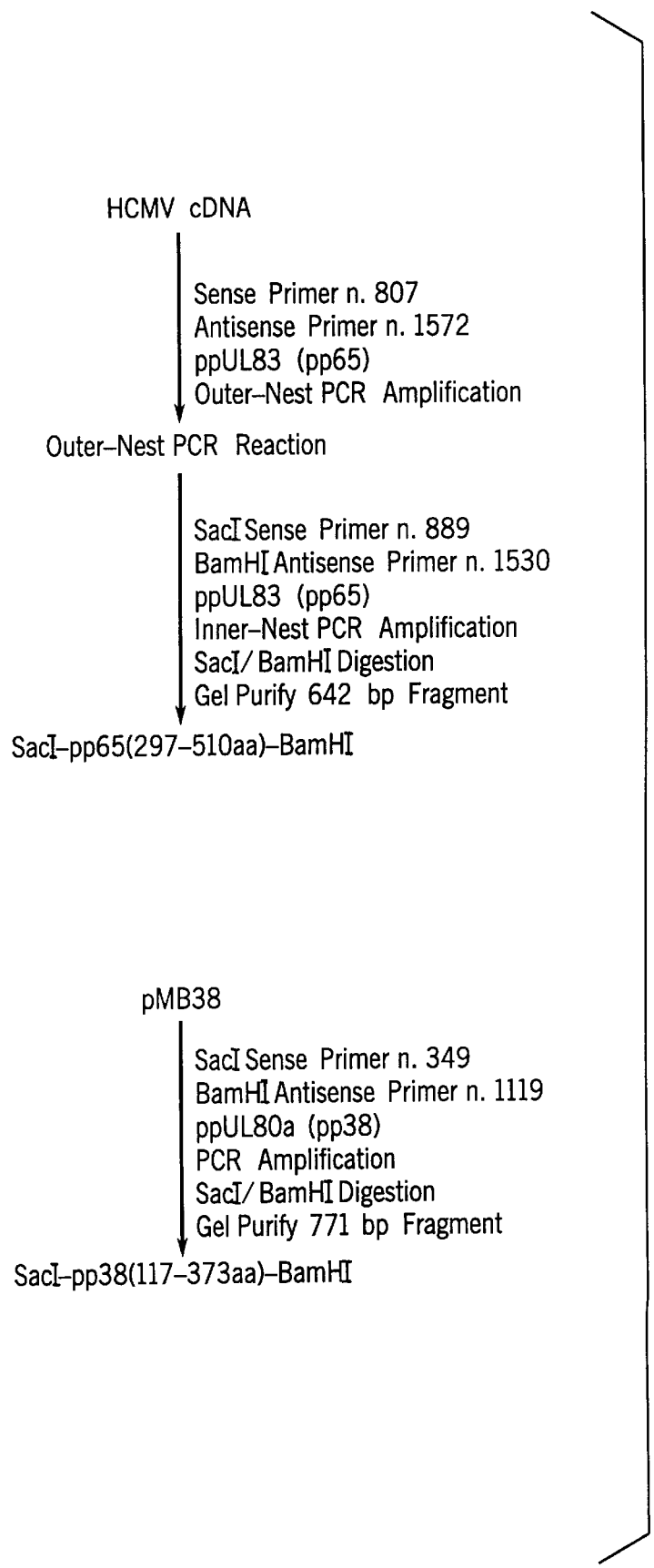
FIG. 13B shows preparation of PCR fragments containing the pp65(297–510aa) and pp38(117–373aa) DNA sequences.
Figure 13C:
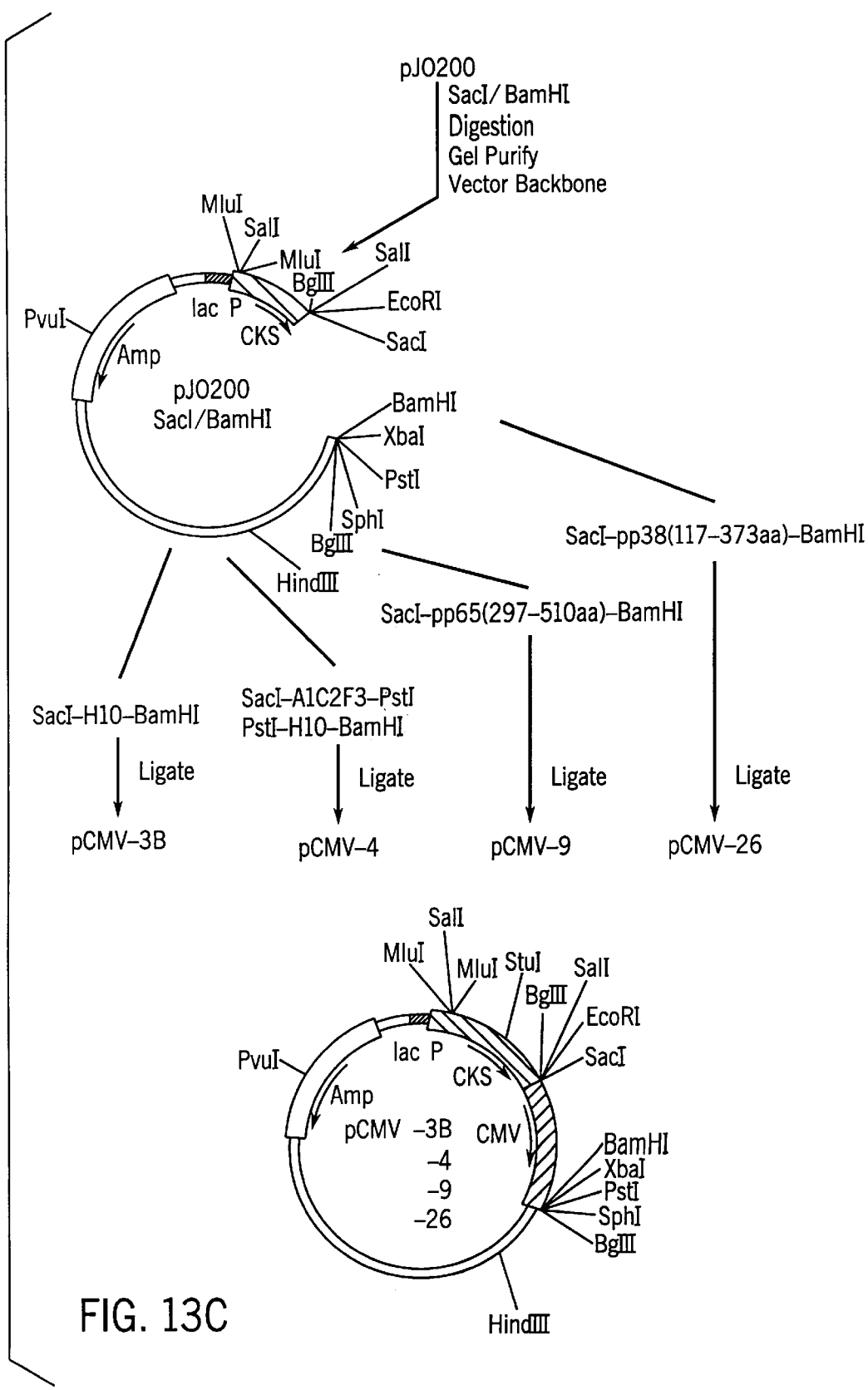
FIG. 13C is a schematic representation of the construction of: plasmid pCMV-3B:CKS-H10, plasmid pCMV-4:CKS-A1C2F3-H10, plasmid pCMV-9:CKS-pp65(297–510aa), and plasmid pCMV-26:CKS-pp38(117–373aa)

The plasmid pCMV-3B is a derivative of plasmid pJO200 (FIGS. 13A and 13C). This plasmid was constructed by cloning a DNA fragment containing HCMV-H10 from plasmid pROSH10, described in Preparation A [see also: Ripalti et al. J. Virological Methods 46: 39, 1994], into pJO200. The H10 DNA sequence is derived from ppUL44 which encodes the phosphoprotein of 52 kD of HCMV. The H10 portion of ppUL44 in pROSH10 contains nucleotides 604–1299 (amino acids 202–434). H10 encodes the C-terminal half of phosphoprotein pp52. Plasmid pCMV-3B was constructed by cloning the H10 DNA fragment from pROSH10, obtained by PCR amplification of the H10 DNA sequence, into the SacI/BamH-I sites of pJO200. Plasmid pJO200 was digested with SacI and BamH-I and the vector backbone was purified on an agarose gel. A sense primer starting at nucleotide 604 of ppUL44 containing a SacI site and an antisense primer starting at nucleotide 1299 of ppUL44 containing a stop codon at the end of the H10 coding sequence and a BamH-I site were synthesized and added to a PCR reaction mixture containing plasmid pROSH10. After PCR amplification, the reaction mixture was digested with SacI and BamH-I, and the 696 base pair fragment containing H10 was purified on an agarose gel and then ligated to pJO200/SacI/BamH-I overnight at 16° C. The next day the ligation mixture was transformed into competent XL-1 Blue cells. Small scale preparation DNA was prepared from the transformants and screened for the presence of the 696 base pair fragment in pJO200 at the SacI/BamH-I sites. Plasmid pCMV-3B, which contains the H10 fragment fused in-frame with the CKS gene, was isolated. The DNA sequence of H10 and the 3' end of the CKS gene was confirmed. This CKS-CMV fusion construct is diagrammed below:

$$\text{CKS(1–248aa)-H10} \qquad (8)$$

C. Construction of pCMV-4: CKS-A1C2F3-H10

The plasmid pCMV-4 is a derivative of pJO200 (FIGS. 13A and 13C). This plasmid was constructed by cloning PCR amplified DNA fragments, containing HCMV-A1C2-K-L-Q-E-F-F3 (briefly: A1C2F3) and HCMV-H10, derived from pMB34 and pROSH1, respectively, into pJO200. Plasmid pJO200 was digested with SacI and BamH-I and the vector backbone was purified on an agarose gel. Into this vector backbone the two PCR-derived DNA fragments will be cloned in a three-way ligation reaction. A1C2-bridge-F3 will be cloned as a SacI/PstI DNA fragment and H10 will be cloned as a PstI/BamH-I DNA fragment. A sense primer starting at nucleotide 1783 of ppUL32 containing a SacI site and an antisense primer starting at nucleotide 3144 of ppUL32 containing an PstI site were synthesized and added to a PCR reaction mixture containing plasmid pMB34. After PCR amplification, the reaction mixture was digested with Sacd and PstI, and the 204 base pair fragment containing A1C2F3 was purified on an agarose gel. A sense primer starting at nucleotide 604 of ppUL44 containing a PstI site and an antisense primer starting at nucleotide 1299 of ppUL44 containing a stop codon at the end of the H10 coding sequence and a BamH-I site were synthesized and added to a PCR reaction mixture containing plasmid pROSH10. After PCR amplification, the reaction mixture was digested with PstI and BamH-I, and the 696 base pair fragment containing H10 was purified on an agarose gel. These purified PCR-derived DNA fragments were then ligated to pJO200/SacI/BamH-I overnight at 16° C. The next day the ligation mixture was transformed into competent XL-Blue cells. Small scale preparation DNA was prepared from the transformants and screened for the presence of A1C2F3 and H10 inserted at the SacI/BamH-I sites of pJO200. Plasmid pCMV-4, which contains A1C2F3 and H10 at the end of the CKS gene in pJO200, was isolated. The DNA sequence of A1 C2-K-L-Q-E-F-F3 and H10 was confirmed. The coding region of the CKS-A1C2F3-H10 construct in pCMV-4 contains a bridge of 2 amino acids contributed from the PstI site between A1C2F3 and H10. This CKS-CMV fusion construct is diagrammed below:

$$\text{CKS(1–248aa)-A1C2-K-L-Q-E-F-F3-L-Q-H10} \qquad (9)$$

D. Construction of pCMV-9: CKS-pp65(297–510aa)

The plasmid pCMV-9 is a derivative of pJO200 (FIGS. 13B and 13C). This plasmid was constructed by cloning a DNA fragment containing HCMV-pp65(297–510aa), obtained by PCR amplification of HCMV cDNA from the region of ppUL83 encoding amino acids 297–510 of pp65 (nucleotides 889–1530), into pJO200. Plasmid pJO200 was digested with SadI and BamH-I and the vector backbone was purified on an agarose gel. A two-stage nested PCR reaction was used to generate the HCMV-pp65(297–510aa) DNA fragment using HCMV cDNA as template, as follows. For the outer nest PCR amplification reaction, a sense primer starting at nucleotide 807 of ppUL83 and an antisense primer starting at nucleotide 1572 of ppUL83 were synthesized and added to a PCR reaction mixture containing HCMV cDNA. After PCR amplification, the outer nest PCR reaction mixture was used as template DNA for the inner nest PCR amplification reaction. For the inner PCR amplification reaction, a sense primer starting at nucleotide 889 of ppUL83 containing a SadI site and an antisense primer starting at nucleotide 1530 of ppUL83 containing a stop codon at the end of the pp65(297–510aa) coding sequence and a BamH-I site, were synthesized and added to a PCR reaction mixture containing outer nest amplified DNA. After PCR amplification, the reaction mixture was digested with SacI and BamH-I, and the 642 base pair fragment containing pp65(297–510aa) was purified on an agarose gel. This purified DNA fragment was then ligated to pJO200/SacI/BamH-I overnight at 16° C. The next day the ligation mixture was transformed into competent XL-Blue cells. Small scale preparation DNA was prepared from the transformants and screened for the presence of pp65 (297–510aa) inserted at the SacI/BamH-I sites of pJO200. Plasmid pCMV-9, which contains pp65(297–510aa) at the end of the CKS gene in pJO200, was isolated. The DNA sequence of pp65(297–510aa) was confirmed. This CKS-CMV fusion construct is diagrammed below:

$$\text{CKS(1–248 aa)-pp65(297–510 aa)} \qquad (10)$$

E. Construction of pCMV-26: CKS-pp38(117–373aa)

The plasmid pCMV-26 is a derivative of pJO200 (FIGS. 13B and 13C). This plasmid was constructed by cloning a DNA fragment containing HCMV-pp 38(117–373aa), obtained by PCR amplification of pp38 DNA from the region of ppUL80a encoding amino acids 117–373 of pp38 (nucleotides 349–1119) derived from pMB38, into pJO200. Large scale plasmid DNA (pMB34) was isolated as described in general methods. Plasmid pJO200 was digested with SacI and BamH-I and the vector backbone was purified on an agarose gel. A sense primer starting at nucleotide 349 of ppUL80a containing a SacI site and an antisense primer starting at nucleotide 1119 of ppUL80a containing a BamH-I site were synthesized and added to a PCR reaction mixture containing pMB38 DNA. After PCR amplification, the reaction mixture was digested with SacI and BamH-I, and the 771 base pair fragment containing pp38(117–373aa) was purified on an agarose gel. This purified DNA fragment was then ligated to pJO200/SacI/BamH-I overnight at 16° C. The next day the ligation mixture was transformed into the competent XL-1 Blue cells. Small scale preparation DNA was prepared from the transformants and screened for the presence of pp38(117–373aa) inserted at the SacI/BamH-I sites of pJO200. Plasmid pCMV-26, which contains pp3B (117–373aa) at the end of the CKS gene in pJO200, was isolated. The DNA sequence of pp38(117–373aa) was confirmed. This CKS-CMV fusion construct is diagrammed below:

$$\text{CKS(1–248aa)-pp38(117–373aa)} \qquad (11)$$

Construction of CKS Epitope-Embedding Expression Vector pEE1

The CKS epitope-embedding expression vector pEE1 allows the embedding of recombinant proteins containing epitopes within the CKS protein as diagrammed below:

$$\text{CKS(1–171aa)- Recombinant Protein -T-R-CKS(171–260aa)} \qquad (12)$$

This pEE1 vector was constructed in two steps starting with the CKS expression vector pJO200. In the first step a mutagenic oligonucleotide is cloned into a pair of adjacent MluI sites located near the 5' end of the CKS gene in pJO200, removing both MluI sites and a SalI site. This modification to pJO200 allows the use of a unique MluI cloning site to be introduced further downstream in the CKS gene in the next step. In the second step a fragment of DNA from pCMV-1 A is cloned into this modified pJO200 vector, thus permitting the embedding of genes as StuI/MluI fragments into the CKS gene.

A. Construction of pJO200-ΔMluI

Figure 14A:
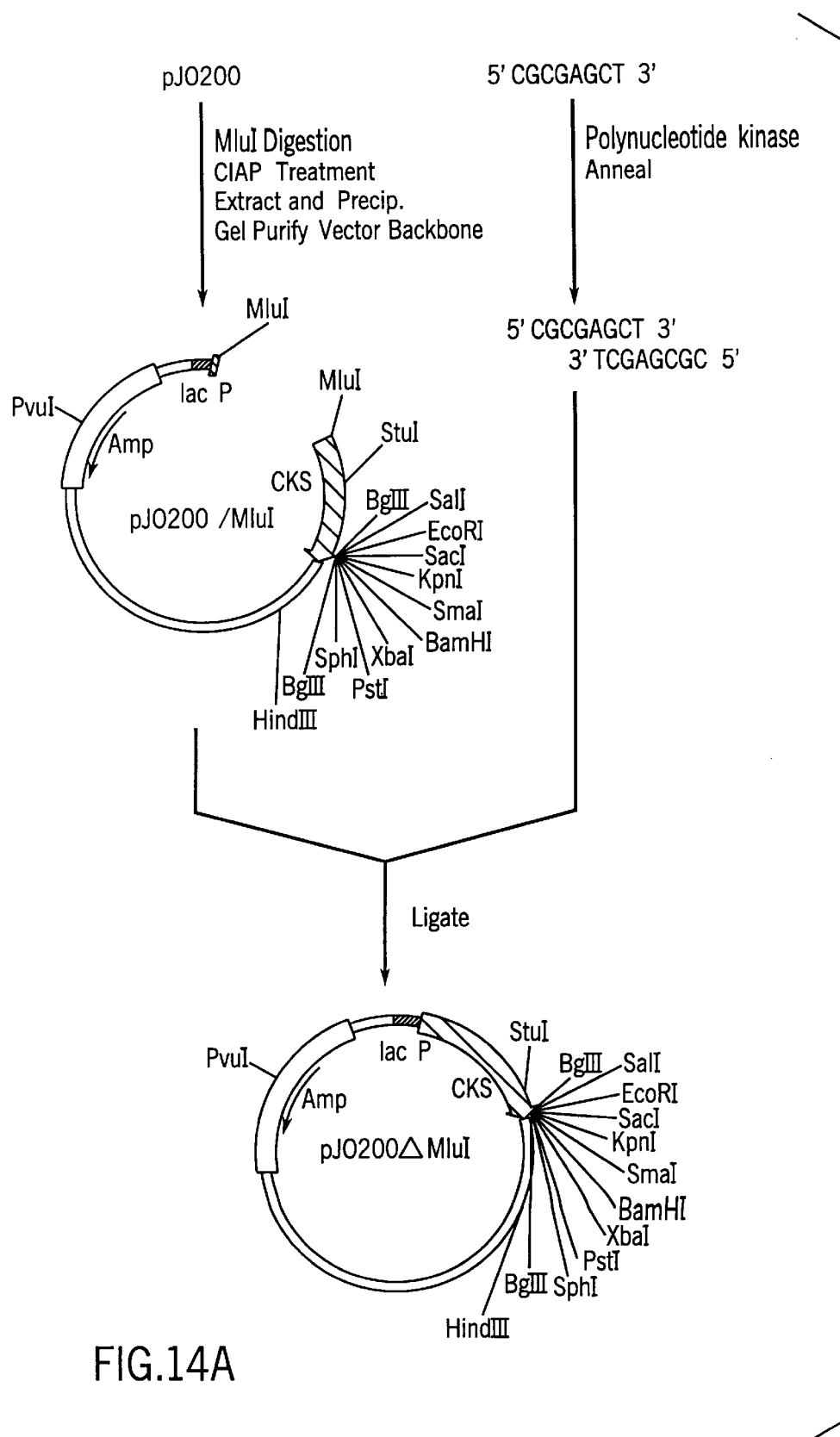
FIG. 14A is a schematic representation of the construction of plasmid pJO200-ΔMluI.

The plasmid pJO200-ΔMluI is a derivative of the CKS expression vector pJO200 (FIG. 14A). This plasmid was constructed by removing a pair of adjacent MluI sites and a SalI site located at nucleotides 161–174 (11–15 amino acids) in the pJO200 DNA sequence shown below using a mutagenic oligonucleotide:

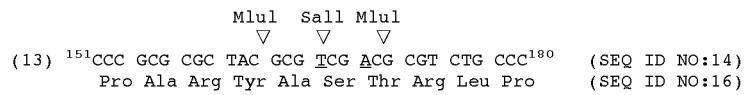

(13) $^{151}$CCC GCG CGC TAC GCG TCG ACG CGT CTG CCC$^{180}$ (SEQ ID NO:14)
Pro Ala Arg Tyr Ala Ser Thr Arg Leu Pro (SEQ ID NO:16)

Native pJO200 DNA sequence nucleotides 151–180 taken in direction 5'→3'

Plasmid pJO200 was digested with MluI and then ethanol precipitated and resuspended in alkaline phosphatase buffer. Plasmid pJO200/MluI was then treated with calf intestinal alkaline phosphatase (CIAP) to remove the 5' phosphate groups to prevent self-ligation. After treatment with CIAP the DNA was extracted with phenol-chloroform, ethanol precipitated, resuspended in TE. buffer, and then the vector backbone was purified on an agarose gel. The following mutagenic oligonucleotide was synthesized in preparation for ligation to pJO200/MluI/CIAP:

This oligonucleotide is self-complementary at its 3' end and will form the following double-stranded structure after a heat denaturation step followed by an annealing step:

This oligonucleotide contains MluI sticky-ends permitting ligation into MluI digested pJO200 DNA. The sequence of this oligonucleotide differs from the native pJO200 DNA sequence in that the "T" and "A" residues underlined in the pJO200 sequence (13) above have been reversed in the mutagenic oligonucleotide as underlined. Thus, the mutagenic oligonucleotide when cloned into the MluI site of pJO200 will destroy both MluI sites and the SalI site. After oligonucleotide synthesis, the synthetic oligonucleotide was phosphorylated at its 5' end using polynucleotide kinase. After treatment with this enzyme, the phosphorylated oligonucleotide was heated to 650C for 20 minutes to inactivate the kinase. After cooling to room temperature, the phosphorylated oligonucleotide was mixed with the pJO200/MluI/CIAP, heated at 65° C. for 5 minutes and then cooled to room temperature gradually to permit annealing of the phosphorylated oligonucleotide to itself. Ligation buffer and T4 DNA ligase were then added to the mixture and incubated overnight at range ol temperatures from 20° C. to 40C. The next day the ligation mixture was transformed into competent XL-1 Blue cells. Small scale preparation DNA was prepared from the transformants and screened for the loss of the MluI and SalI sites. Plasmid pJO200ΔMluI, which has lost these restriction enzyme sites, was isolated. The DNA sequence of the 5' end of the CKS gene was confirmed. In addition to removing the MluI and SalI sites, the mutagenic oligonucleotide changes the amino acids coded by nucleotides 166–171 from Ser-Thr to Thr-Ser as shown below:

(SEQ ID NO: 15) Pro Ala Arg Tyr Ala Thr Ser Arg Leu Pro
(SEQ ID NO: 17) (13')

pJO200ΔMluI DNA sequence nucleotides 151–180 taken in direction 5-3'

B. Construction of pEE1 30

Figure 15:
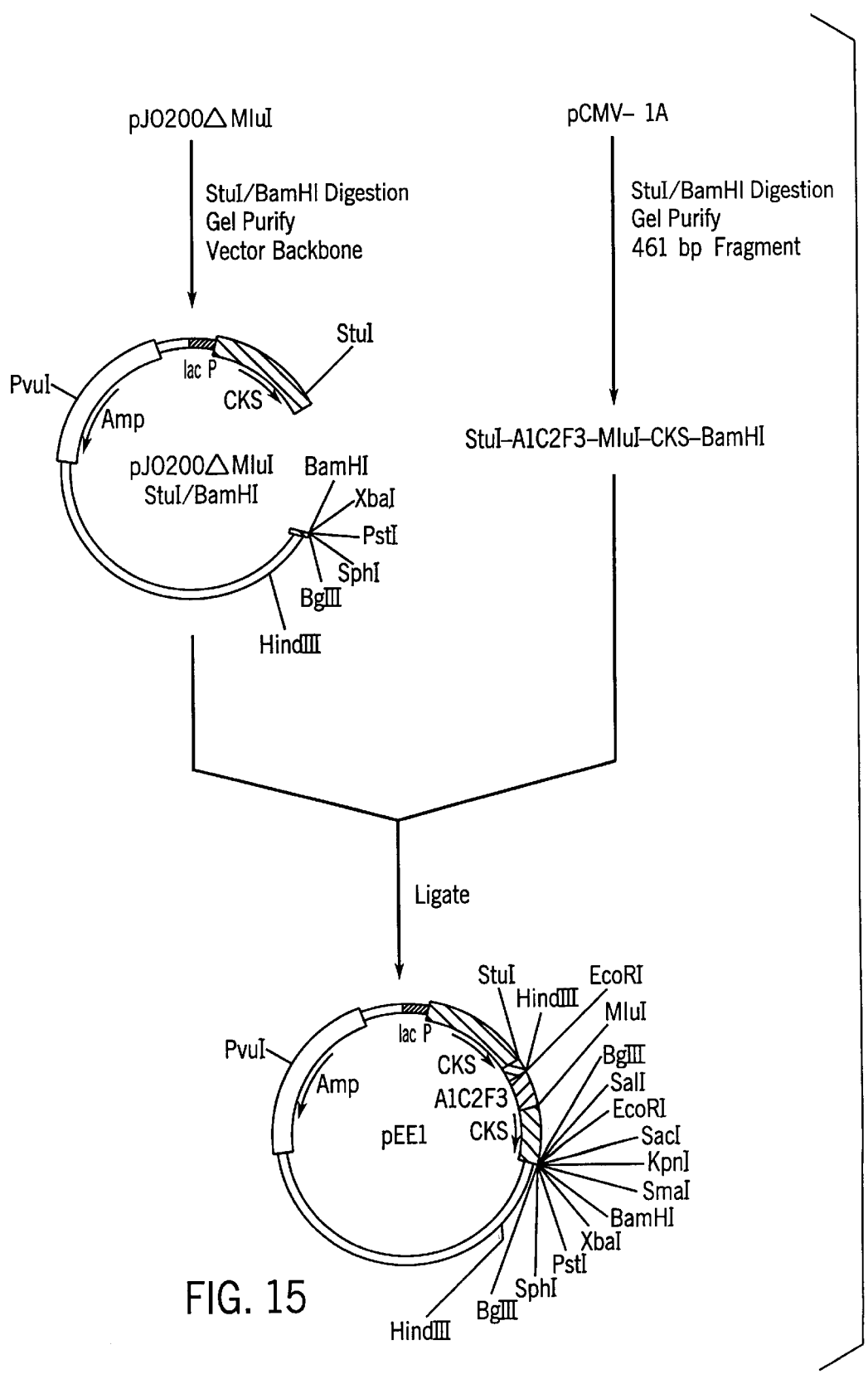
FIG. 15 is the schematic representation of the construction of plasmid pEE1.

The plasmid pEE1 is a derivative of the plasmid pJO200ΔMluI (FIG. 15). This plasmid was constructed by cloning a StuI/BamH-I fragment from pCMV-1 A, which contains HCMV-A1 C2F3 embedded within the CKS gene, into the StuI/BamH-I sites of pJO200ΔMluI. By substituting the StuI/BamH-I DNA fragment within the CKS coding region present in pJO200ΔMluI with the StuI/BamH-I fragment from pCMV-1 A, the resulting plasmid pEE1 contains HCMV-A1 C2F3 embedded within the CKS gene. Plasmid pEE1 differs from plasmid pCMV-1A in that pEE1 does not contain the upstream MluI sites present in the 5' end of the CKS gene. Hence, digestion of pEE1 with StuI and MluI will release the HCMV-A1C2F3 DNA fragment and provide a vector backbone, after purification on an agarose gel, capable of accepting other genes for embedding into the CKS gene as blunt/MluI compatible sticky-end DNA fragments. Large scale plasmid DNAs (pJO200ΔMluI and pCMV-lA) were isolated as described in general methods. Plasmid pCMV-1 A was digested with StuI and BamH-I and the 461 base pair fragment, containing A1C2F3 and the 3' end of the CKS gene, was purified on an agarose gel. Plasmid pJO200ΔMluI was digested with StuI and BamH-I and the vector backbone was; purified on an agarose gel. These purified DNA fragments were then mixed together and ligated overnight at 16° C. The next day the ligation mixture was transformed into competent XL-1 Blue cells. Small scale preparation DNA base prepared from the transformants and screened for the presence of the 461 base pair A1C2F3 DNA fragment in pJO200ΔMluI. Plasmid pEE1, which contains the A1C2F3 DNA fragment and no MluI sites in the 5' end of the CKS gene, was isolated. The DNA sequence of the 3' end of the CKS gene and the A1C2F3 fragment was confirmed. Digestion of plasmid pEE1 with StuI and BamH-I followed by purification of the vector backbone on an agarose gel removes the A1C2F3 DNA fragment completely in preparation for ligation with other DNA fragments. This purified vector backbone can accept DNA fragments for embedding into the CKS gene in the correct reading frame in the following format:

5' X- Gene of interest -Y 3' (16)

where X is a blunt end and Y is an MluI compatible sticky-end, for example MluI or BssHII.

Construction of CKS-epitope-embedding Expression vectors based on pEE1 (Preparation F)

The CKS expression vector pEE1 is the building block for a series of three CKS-CMV-CKS gene fusion constructs. For each construct plasmid pEE1 was digested with StuI and MluI and the vector backbone was purified. This backbone is ready to accept CMV gene fragments generated by PCR which have a StuI site at their 5' end and a MluI site at their 3' end. After digestion with StuI and MluI, the PCR fragments are cloned in-frame into the pEE1/StuI/MluI backbone. The CKS-CMV-CKS fusion proteins expressed from these vectors are diagrammed below where T and R are the threonine and arginine residues, respectively, encoded by the synthetic MluI site introduced into the vector CKS(1–171 aa)-CMV-T-R-CKS(171–260 aa)　　　(17)

A. Construction of pCMV-27: CKS-A1C2F3-H10-CKS

Figure 16A:
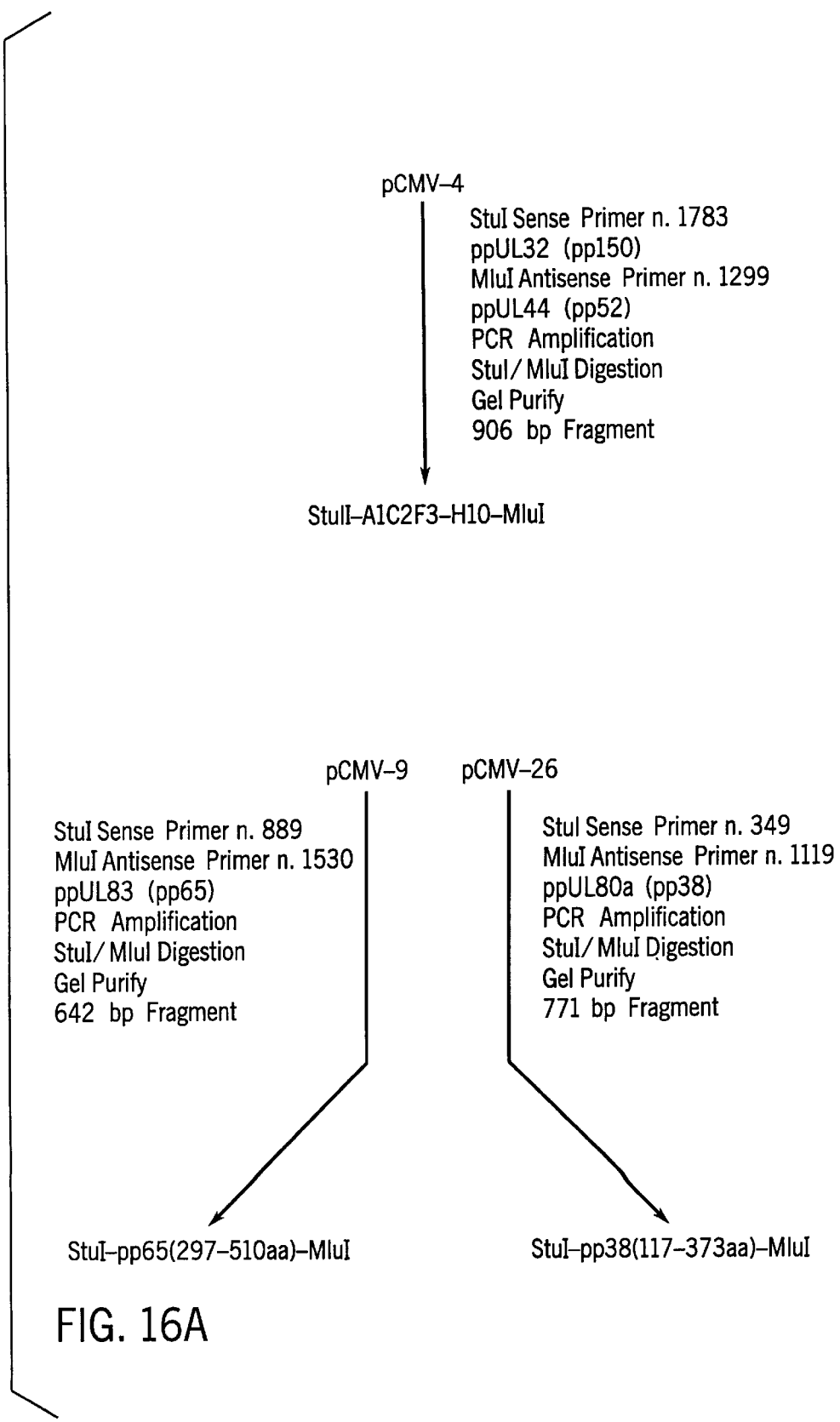
FIG. 16A shows the preparation of PCR fragments containing the A1C2F3-H10, pp65(297–510aa), and pp38 (117–373aa) DNA sequences.
Figure 16B:
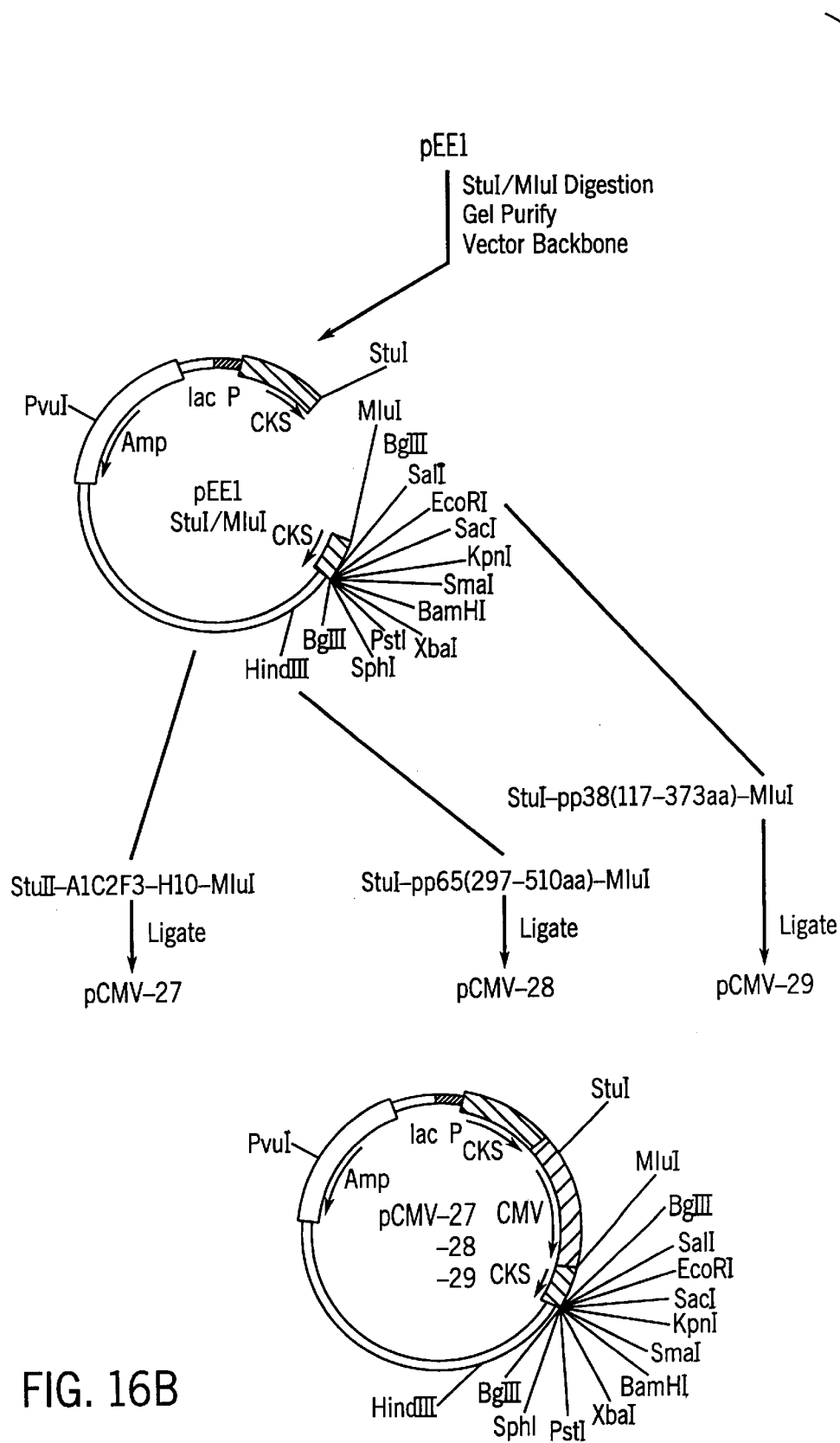
FIG. 16B is a schematic representation of the construction of: plasmid pCMV-27:CKS-A1C2F3-H10-CKS, plasmid pCMV-28:CKS-pp65(297–510aa)-CKS, and plasmid pCMV-29:CKS-pp38(117–373aa)-CKS.

The plasmid pCMV-27 is a derivative of pEE1 (FIGS. 16A and 16B). This plasmid was constructed by cloning a PCR amplified DNA fragment, containing HCMV-A1 C2F3-H10 derived from pCMV-4 (therefore containing the bridge KLQEF between A1C2 and F3), into pEE1. Large scale plasmid DNA (pEE1 and pCMV-4) was isolated operating as described in General Methods. Plasmid pEE1 was digested with StuI and MluI and the vector backbone was purified on an agarose gel. A sense primer starting at nucleotide 1783 of ppUL32 containing a StuI site and an antisense primer starting at nucleotide 1299 of ppUL44 containing an MluI site were synthesized and added to a PCR reaction mixture containing plasmid pCMV-4. After PCR amplification, the reaction mixture was digested with StuI and MluI, and the 906 base pair fragment containing A1C2F3-H10 was purified on an agarose gel. This purified DNA fragment was ligated to pEE1/StuI/MluI overnight at 16° C. The next day the ligation mixture was transformed into competent XL-1 Blue cells. Small scale preparation DNA was prepared from the transformants and screened for the presence of the A1C2F3-H10 DNA fragment inserted at the StuI/MluI sites of pEE1. Plasmid pCMV-27, which contains A1C2F3-H10 embedded at the StuI/MluI sites of pEE1, was isolated. The DNA sequence of A1C2F3-H10 and the adjacent DNA sequence of CKS was confirmed. See SEQ ID NO: 3 and SEQ ID NO: 4. This CKS-CMV-CKS fusion construct is diagrammed below, where L, Q and T, R are the leucine, glutamine and threonine, arginine residues, respectively, encoded by the synthetic PstI and MluI sites introduced into the vector:

CKS(1–171 aa)-A1C2-K-L-Q-E-F-F3-L-Q-H10-T-R-CKS(171–260 aa)　　　(18)

B. Construction of pCMV-28: CKS-pp65 (297–510aa)-CKS

The plasmid pCMV-28 is a derivative of pEE1 (FIGS. 16A and 16B). This plasmid was constructed by cloning a PCR amplified DNA fragment, containing HCMV-pp65 (297–510aa) derived from CMV-9, into pEE1. Large scale plasmid DNAs (pEE1 and pCMV-9) were isolated by general methods. Plasmid pEE1 was digested with StuI and MluI and the vector backbone was purified on an agarose gel. A sense primer starting at nucleotide 889 of ppUL83 containing a StuI site and an antisense primer starting at nucleotide 1530 of ppUL83 containing an MluI site were synthesized and added to a PCR reaction mixture containing plasmid pCMV-9. After PCR amplification, the reaction mixture was digested with StuI and MluI, and the 642 base pair fragment containing pp65(297–510aa) was purified on an agarose gel. This purified DNA fragment was ligated to pEE1/StuI/MluI overnight at 16° C. The next day the ligation mixture was transformed into competent XL-1 Blue cells. Small scale preparation DNA was prepared from the transformants and screened for the presence of the pp65 (297–510aa) DNA fragment inserted at the StuI/MluI sites of pEE1. Plasmid pCMV-28, which contains pp65 (297–510aa) embedded at the StuI/MluI sites of pEE1, was isolated. The DNA sequence of pp65(297–510aa) and the adjacent DNA sequence of CKS was confirmed. This CKS-CMV-CKS fusion construct is diagrammed below where T and R are the threonine and arginine residues, respectively, encoded by the synthetic MluI sites introduced into the vector:

CKS(1–171 aa)-pp65(297–510aa)-T-R-CKS(171–260aa)　　　(19)

C. Construction of pCMV-29: CKS-pp38 (117–373aa)-CKS

The plasmid pCMV-29 is a derivative of pEE1 (FIGS. 16A and 16B). This plasmid was constructed by cloning a PCR amplified DNA fragment, containing HCMV-pp38 (117–373aa) derived from pCMV-26, into pEE1. Large scale plasmid DNA (pEE1 and pCMV-26) was isolated as described in general methods. Plasmid pEE1 was digested with StuI and MluI and the vector backbone was purified on an agarose gel. A sense primer starting at nucleotide 349 of ppUL80a containing a StuI site and an antisense primer starting at nucleotide 1119 of ppUL80a containing an MluI site were synthesized and added to a PCR reaction mixture containing plasmid pCMV-26. After PCR amplification, the reaction mixture was digested with StuI and MluI, and the 771 base pair fragment containing pp38(117–373aa) was purified on an agarose gel. This purified DNA fragment was ligated to pEE1/StuI/MluI overnight at 16° C. The next day the ligation mixture was transformed into competent XL-I Blue cells. Small scale preparation DNA was prepared from the transformants and screened for the presence of the pp38(117–373aa) DNA fragment inserted at the StuI/MluI sites of pEE1. Plasmid pCMV-29, which contains pp38(117-373aa) embedded at the StuI/MluI sites of pEE1, was isolated. The DNA sequence of pp38(117–373aa) and the adjacent DNA sequence of CKS was confirmed. This CKS-CMV-CKS fusion construct is diagrammed below where 1 and R are the threonine and arginine residues, respectively, encoded by the synthetic MluI sites introduced into the vector:

CKS(1–171 aa)-pp38(117–373aa)-T-R-CKS(171–260 aa)　　　(20)

Production of Recombinant CMV Antigens (Preparation G)

A. Expression of HCMV genes

Bacterial clones expressing HCMV fusion proteins of Preparation F, the control bacterial strain expressing unfused CKS, and bacterial clones expressing HCMV fusion proteins of Preparation E, were grown in "SUPERBROTH II" media containing 100 µg/ml ampicillin to log phase and the synthesis of the CKS-HCMV fusion proteins was induced by the addition of IPTG as described in Robinson I M, Pilot-Matias T I, Pratt S D, Patel C B, Bevirt T S, Hunt J C. Analysis of the humoral response to the flagellin protein Borrelia burgdoeferi; cloning of regions capable of differentiating lyme disease from syphilis. J Clin Microbiol 1993; 31: 629–635. After 4 hours post-induction, the cells were harvested and the cell pellets were stored at −80° C. until protein purification. The relevant data of all the expressed proteins are given in Table 3.

B. Purification of unfused CKS and recombinant CKS-HCMV fusion proteins

Insoluble CKS-HCMV fusion proteins (rpCMV-1A, rpCMV-3B, rpCMV-4, rpCMV-9, rpCMV-27, rpCMV-28, rpCMV-29) were purified after lysis by a combination of detergent washes that were followed by solubilization in 8M urea. After solubilization in 8M urea, the fusion proteins were purified by Q-Sepharose chromatography (Pharmacia Biotech, Piscataway, N.J.). Fusion protein 4 (rpCMV-4) and 9 (rpCMV-9) were subjected to additional purification by Sephacryl S-200 chromatography (Pharmacia Biotech, Piscataway, N.J.). Soluble CKS-HCMV fusion protein 26 (rpCMV-26) was purified after cell lysis on preparative SDS-PAG using a BIO-Rad Prep Cell (Bio-Rad, Richmond, Calif.). Insoluble fusion proteins (rpCMV-27, rpCMV-28, rpCMV-29) were also purified by a combination of detergent washes, which were followed by solubilization in 1% SDS and then further purified by Sephacryl S-300 HR chromatography (Pharmacia Biotech, Piscataway, N.J.). Soluble CKS protein was purified after cell lysis by ammonium sulfate precipitation followed by DEAE chromatography.

EXAMPLES

Comparative Example A

Automated HCMV IgM Immunoassay

The use of recombinant polypeptides, which contain epitopes within the ppUL32, ppUL44, ppUL83, and ppUL80a regions of the HCMV genome, provide immunological assays that have increased sensitivity and that may be more specific than HCMV IgM immunoassays using epitopes from the virus. In the automated HCMV IgM immunoassay, three E.Coli expressed recombinant proteins, CKS-A1C2F3-H10-CKS (rpCMV-27), CKS-pp65-CKS (rpCMV-28), and CKS-pp38-CKS (rpCMV-29), representing four distinct regions of the HCMV genome were used. Each of these recombinant polypeptides were prepared according to Preparation F (A, B, and C) and Preparation G (A and B). In the automated immunoassay, each of these three recombinant antigens were coated separately onto polystyrene microparticles, one antigen per microparticle. The automated immunoassay can then be run in either a sequential mode of operation or in a combination mode of operation. In a modification of the automated immunoassay, two of the three recombinant antigens (rpCMV-27 and rpCMV-29) can be coated together onto the same polystyrene microparticle and then blended with microparticles coated with the third recombinant antigen (rpCMV-28). The modified automated immunoassay can then be run in a combination mode of operation.

The polystyrene microparticles (2.65 µm size) in distilled water were introduced into a solution containing 50 mM Tris, 137 mM sodium chloride, 0.1% sodium azide, pH 7.5. The polystyrene microparticles were then dispensed into three separate bottles designated rpCMV-27, rpCMV-28, and rpCMV-29. Recombinant rpCMV-27 in 50 mM Tris, pH 8.5 was added to the bottle containing rpCMV-27 to give a final concentration of 100 µg/ml.

Recombinant rpCMV-28 in 50 mM Tris, pH 8.5 was added to the bottle containing rpCMV-28 to give a final concentration of 100 µg/ml. Recombinant rpCMV-29 in 50 mM Tris, pH 8.5 was added to the bottle containing rpCMV-29 to give a final concentration of 100 µg/ml. The final concentration of the polystyrene microparticles in each bottle was 1–3% solids. The bottles were rotated end over end (30–50 rpm) for two hours at room temperature (19–22° C.) and were then centrifuged at 10,000–15,000× g for 10 minutes at room temperature. The microparticles, which were in the form of pellets, were then resuspended in a mixture containing 90 mM Tris, 135 mM sodium chloride, 100 mM disodium EDTA, 6% sucrose, 0.18% "TWEEN-20", 50% fetal calf serum (CMV antibody free), 35 mg/ml CKS protein, pH 7.5 to give a final concentration of 0.1–0.25% solids. The microparticles were then loaded into plastic bottles.

The polystyrene microparticles coated with rpCMV-27 rpCMV-28, and rpCMV-29 were used in an antibody capture format in an automated immunoassay performed on the ABBOTT "IMx" instrument (Abbott Laboratories, Abbott Park, Ill.). The aforementioned coated microparticles can also be used in an antibody capture format in an automated immunoassay performed on the Abbott "AxSYM" instrument (Abbott Laboratories, Abbott Park, Ill.).

These systems employ pipetting devices that dispense serum samples and reagents automatically. These instruments employ an optical reader that can measure the fluorescence emission reflectance at 448 nm from the sample matrix. In the sequential mode of operation, the serum sample is incubated separately with each of the three coated microparticles. In the combination mode of operation, an equal volume of each of the three coated microparticles are mixed together prior to incubation with the serum sample. In either mode the appropriate stock microparticles are dispensed into plastic bottles and then are loaded onto the instrument.

The preferred conjugate is goat anti-human IgM alkaline phosphatase conjugate. The conjugate is titered to determine a working concentration of 0.2–1.5 µg/ml. The conjugate diluent includes 90 mM Tris, 135 mM sodium chloride, 5% fetal calf serum, 0.1% sodium azide, pH 7.4. The conjugate is sterile filtered, filled in plastic bottles, and loaded onto the instrument. The preferred substrate for the conjugate is 4-methylumbelliferyl phosphate.

Anti-HCMV positive index calibrator is prepared from plasma units positive for antibodies to HCMV. The pooled units are recalcified, aliquoted, and stored at −20° C. or at 2–8° C. For each lot of positive Index calibrator, the stock solution is diluted with negative control containing 0.1% sodium azide as a preservative. The final material is sterile filtered and filled in plastic bottles.

Anti-HCMV negative control is prepared from recalcified human plasma negative for antibodies to HCMV. The plasma is also negative for antibodies to human immunodeficiency virus (HIV) and negative for hepatitis B surface antigen (HBsAg). The units are pooled, and 0.1% sodium azide is added as a preservative. The final material is sterile filtered and filled in plastic bottles.

The serum samples to be tested are dispensed into the instrument's reaction vessels. The appropriate code to run the automated CMV IgM immunoassay is entered and then the assay is begun. The instrument dilutes the serum sample in line diluent (0.1 M sodium phosphate, 0.1% sodium azide, pH 7.5 or 0.3 M sodium chloride, 0.1 M Tris, 0.1% sodium azide, pH 7.5) and then adds the microparticles to the diluted serum sample. After incubation for 5–10 minutes, the mixture is then transferred to the reaction vessel matrix. The matrix is washed with line diluent and then the conjugate is added to the reaction vessel matrix. After incubation for 8–10 minutes, the matrix is washed with line diluent and then the substrate for the conjugate is added. The fluorescence emission reflectance at 448 nm from the sample matrix is read immediately and the instrument reports both a rate count value and an index value for each sample. The index value is equal to the rate count value for the sample divided by the rate count value for the positive index calibrator. In order to maintain acceptable assay specificity, the cut-off value for the assay should be at least 3–4 standard deviations above the mean of the index values for the negative samples. The cut-off value for the automated HCMV IgM immunoassay was set at an index value of 0.6. Samples with an index value equal to or greater than 0.6 were considered positive for HCMV IgM antibody. Samples with an index value of 0.500–0.599 were considered equivocal, and samples with an index value less than 0.500 were considered negative for HCMV IgM antibody. The characteristics of the fusion proteins used in the assay are referred to in Table 3.

The following examples show which component of the assay for HCMV IgM antibodies is the component that is responsible for bringing about false positive results in the determination of HCMV infection and how the level of false positive results can be reduced.

Example 1

In order to construct the immunoassay of the present invention, it was first necessary to determine what component of the AxSYM HCMV IgM immunoassay of U.S. Ser. No. 08/765,856 was contributing to the lack of diagnostic assay specificity. Serum specimens from random blood donors (low risk population, 308 donors) were tested with three commercially available HCMV IgM immunoassays (consensus assays) and with the AxSYM HCMV IgM immunoassay described in U.S. Ser. No. 08/765,856 to isolate the factor that resulted in indicating false positive results. Serum specimens determined to be positive (three specimens), equivocal (two specimens), and negative (four specimens) by the consensus assays were selected for further study.

Three different classes of coated microparticles were then prepared with different combinations of the following recombinant HCMV antigens:

| | |
|---|---|
| H10/A1C2/F3 | CKS(1–171aa)-A1C2/F3-H10-CKS(171–260aa) A1C2(595–614aa), F3(1006–1048aa) (UL32) H10(202–434aa) (UL44) |
| H10 | CKS(1–171aa)-H10-CKS(171–260aa) H10(202–434aa) (UL44) |
| pp65 | CKS(1–171aa)-pp65-CKS(171–260aa) pp65(297–510aa) (UL83) |
| pp38 | CKS(1–171aa)-pp38-CKS(171–260aa) pp38(117–373aa) (UL80a) |

The following coatings for microparticles were prepared:

| | |
|---|---|
| Coating no. 1 (AH only) | Microparticles coated with the H10/A102/F3 antigen only |
| Coating no. 2 (H only) | Microparticles coated with the H10 antigen only |
| Coating no. 3 (Complete) | Microparticles coated with the H10/A1C2/F3, pp65 and pp38, antigens (rpCMV27, rpCMV28, rpCMV29) |

In three separate experiments, the specimens in TABLE I were tested on the automated "AxSYM" instrument using the same assay protocol with reagent packs containing the three foregoing types of microparticles. The rate counts obtained from the specimens using the three different coated microparticles are listed in TABLE I. The cutoff for the assays in these experiments was approximately 250 rate counts.

As can be seen from the specimens 132 and 221 (Negative for HCMV IgM antibody by consensus, Positive for HCMV IgM antibody by "AxSYM" instrument) and specimens 177 and 215 (Equivocal for HCMV IgM antibody by consensus, Positive for HCMV IgM antibody by "AxSYM"

instrument), the contribution of the positive signal on the "AxSYM" instrument was derived solely from the H10/A1C2/F3 antigen coated microparticles (compare the signal provided by coating no. 1 (AH microparticles) with the signal provided by coating no. 3 (complete microparticles)). In each of these four specimens, the AH microparticles provided approximately the same amount of signal as did the complete microparticles, thereby narrowing the analysis to the microparticles coated with H10/A1C2/F3 antigen. The component contributing to the lack of diagnostic assay specificity was further identified as the A1C2/F3 antigen, because the H10 antigen alone contributed no positive signal in these four specimens (compare signal provided by coating no. 1 (AH microparticles) with the signal provided by coating no. 2 (H microparticles)).

TABLE I

POSITIVE SIGNAL ON RANDOM BLOOD DONOR CONTRIBUTED PRIMARILY FROM SERUM IgM ANTIBODY AGAINST A1C2F3

| Specimen | Consensus[1] | AH Microparticles (Coating no.[1]) | H Microparticles (Coating no.[2]) | AH, 65, 38 Microparticles (Coating no.[3]) |
|---|---|---|---|---|
| 8466 | Positive | 1853 | 1904 | 1526 |
| UT32544 | Positive | 877 | 731 | 586 |
| 127 | Negative | 11 | 76 | 238 |
| 132 | Negative | 1639 | 55 | 1342 |
| 155 | Positive | 953 | 71 | 1011 |
| 177 | Equivocal | 596 | 18 | 519 |
| 215 | Equivocal | 839 | 61 | 1035 |
| 220 | Negative | 84 | 66 | 373 |
| 221 | Negative | 585 | 56 | 434 |

[1]The consensus determination was based on three commercially available IgM immunoassays. If two out of three of the assays indicated a given result, that result was assumed to be the correct result.

The data in TABLE I indicate that the excessive number of false positives was caused by the A1C2F3 portion of the fusion protein H10/A1C2/F3.

Example 2

After the A1C2F3 portion of the fusion protein was identified as the cause of poor assay specificity, the amount of H10/A1C2F3 coated microparticles in the "AxSYM" HCMV IgM assay described in U.S. Ser. No. 081765,856 was reduced by approximately 2 to 3-fold. Two reagent packs containing the complete antigen cocktail were then prepared. The reagent packs differed only. in the concentration of microparticles coated with H10/A1C2F3 antigen. The reagent pack labelled "AxSYM Normal" contained coated microparticles at the normal concentration and the reagent pack labelled "AxSYM Reduced AH" contained reduced concentrations (2–3 fold) of microparticles coated with H10/A1C2F3 antigen with normal concentrations of microparticles coated with pp65 and pp38.

Serum specimens from random blood donors (low risk population, 308 donors) were then tested on the automated "AxSYM" instrument in separate experiments using the same assay protocol with both reagent packs. Using the same assay cutoff (0.6) and Index Calibrator with both reagent packs, the assay using the "AxSYM Normal" reagent pack determined that 9.7% of the specimens were positive for HCMV IgM antibody, whereas the assay using the "AxSYM Reduced AH" reagent pack determined that 2.3% of the specimens were positive for HCMV IgM antibody. The consensus assays described in EXAMPLE 1 determined that 1.6% of the specimens were positive for HCMV IgM antibody. Therefore, reduction of the concentration of microparticles coated with H0/A1C2/F3 antigen in the "AxSYM" HCMV IgM assay significantly improved assay specificity in good agreement with the consensus assays.

The next step was to determine if the sensitivity of the "AxSYM" HCMV IgM assay with the reduced level of microparticles coated with H10/A1C2F3 was affected by the reduction in antigen by testing patient specimens with different amounts of HCMV-specific IgM antibodies as determined by the consensus assays (Sensitivity Panel). Serum specimens from the sensitivity panel were then tested on the automated "AxSYM" instrument in separate experiments using the same assay protocol with both reagent packs ("AxSYM Normal" and "AxSYM Reduced AH"). The same assay cutoff (0.6) and Index Calibrator were used with both reagent packs and the results are set forth in TABLE II.

TABLE II

SENSITIVITY PANEL

| Specimen | Consensus | "AxSYM Normal" | "AxSYM Reduced AH" |
|---|---|---|---|
| 51 | Positive | 1.187 | 0.380 |
| 84 | Positive | 3.842 | 1.024 |
| 85 | Positive | 2.071 | 0.358 |
| 113 | Positive | 1.679 | 0.303 |
| 149 | Positive | 1.229 | 0.052 |
| 184 | Positive | 0.626 | 0.156 |
| 202 | Positive | 0.651 | 0.229 |
| 93 | Equivocal | 0.832 | 0.270 |
| 188 | Equivocal | 0.299 | 0.206 |
| 63 | Negative | 0.315 | 0.108 |

Of the seven specimens determined to be positive for HCMV IgM antibody by the consesus assays, the protocol utilizing the "AxSYM Normal" reagent pack also determined that all seven specimens were positive for HCMV IgM antibody whereas only one of the seven specimens were determined positive for HCMV IgM antibody by the "AxSYM Reduced AH" reagent pack. Therefore, reduction of H10/A1C2/F3 antigen improves assay specificity but results in deterioration of assay sensitivity.

Example 3

The results of Example 2 clearly demonstrated that lowering the amount of the H10/A1C2/F3 coated microparticles improved assay specificity at the expense of assay sensitivity. In order to improve the specificity of the "AxSYM" HCMV IgM assay described in U.S. Ser. No. 08/765,856, the effect of adding A1C2 and F3 synthetic peptides to the microparticle diluent in limiting amounts in this assay was examined to determine if the low level of IgM present in patient specimens not indicative of an acute or recent HCMV infection could be selectivity and competitively inhibited by the presence of these peptides.

Synthetic peptides A1C2 (20mer) and F3 (43mer) were added to the microparticle diluent in equal amounts each at the following concentrations: 0, 0.1, 1.0, 10, and 25 µg/ml. Control positive panel serum specimens obtained from individuals with a recent HCMV infection (Pos Panel No, 1–4) and selected random blood donor (RBD Panel No. 1–4) were run to determine if the peptides can selectively lower the signal on random blood donor specimens (low risk population). The rate counts obtained from the specimens using the different levels of peptide in the microparticle diluent are set forth in TABLE III. The cutoff for the assays in these experiments is approximately 250 rate counts.

TABLE III

| Specimen | Rate counts Obtained at Different Concentrations of A1C2 and F3 | | | | |
|---|---|---|---|---|---|
| | 0 µg/ml | 0.1 µg/ml | 1.0 µg/ml | 10 µg/ml | 25 µg/ml |
| Pos Panel No. 1 | 652 | 657 | 662 | 735 | 782 |
| Pos Panel No. 2 | 729 | 699 | 728 | 780 | 836 |
| Pos Panel No. 3 | 1696 | 1601 | 1616 | 1853 | 1994 |
| Pos Panel No. 4 | 1184 | 1203 | 1131 | 1277 | 1302 |
| RBD Panel No. 1 | 360 | 294 | 256 | 170 | 179 |
| RBD Panel No. 2 | 406 | 246 | 212 | 147 | 106 |
| RBD Panel No. 3 | 257 | 161 | 139 | 79 | 61 |
| RBD Panel No. 4 | 231 | 194 | 194 | 199 | 182 |

The signals from the positive panel specimens (Pos Panel Nos. 1–4) were not affected by the presence of the A1C2 and F3 peptides in the microparticle diluent. At the highest concentrations of peptide, a modest increase in signal is observed with some of the positive panel specimens. In contrast, the signal from random blood donors specimens is reduced in the presence of the A1C2 and F3 peptides in the microparticle diluent up to a concentration of 10 µg/ml. Three of the specimens (RBD Panels No. 1, No. 2, and No. 3) were determined to be negative for HCMV IgM antibody after addition of these peptides to the microparticle diluent. Further experiments were conducted with these and other panel members to determine the optimum amount of each peptide in the microparticle diluent that would minimize the negative impact on signals from positive specimens obtained from individuals with an acute or recent HCMV infection and maximize the negative impact on signals from random blood donor specimens obtained from individuals who do not have an acute or recent HCMV infection. The concentration ranges employed for each peptide were from 1 to 12 µg/ml. The optimum amount of each peptide was determined to be 6 µg/ml in the microparticle diluent containing HCMV recombinant antigen coated microparticles (Coating No. 3, Example 1) at a concentration of 0.2% solids.

After the concentration of peptides in the microparticle diluent was optimized, the improved "AxSYM" HCMV IgM assay of this invention was further tested on the same random blood donor specimens as previously tested and the performance compared to the performance of the "AxSYM" HCMV IgM assay described in U.S. Ser. No. 081765,856, which did not contain the peptides A1C2 and F3 in the microparticle diluent. The improved "AxSYM" HCMV IgM assay determined that 3.3% of the specimens were positive for HCMV IgM antibody whereas the "AxSYM" HCMV IgM assay described in U.S. Ser. No. 08/765,856 determined that 9.7% of the specimens were positive for HCMV IgM antibody. The addition of peptide resulted in a 3-fold reduction in the number of positive specimens determined to be positive for HCMV IgM antibody, which is much closer to the consensus number of 1.6%. The "AxSYM" HCMV IgM assay of this invention has significantly improved diagnostic assay specificity over the previous assay described in U.S. Ser. No. 08/765,856.

The "AxSYM" HCMV IgM assay of this invention was also tested with the same sensitivity panel members described in Example 2, TABLE II, and the performance compared with the performance of The "AxSYM" HCMV IgM assays described in U.S. Ser. No. 08/765,856. The results are set forth in TABLE IV.

TABLE IV

| Specimen | Expected result | "AxSYM" | "AxSYM" This invention |
|---|---|---|---|
| 51 | Positive | 1.187 | 1.102 |
| 84 | Positive | 3.842 | 3.295 |
| 85 | Positive | 2.071 | 1.275 |
| 113 | Positive | 1.679 | 1.408 |
| 149 | Positive | 1.229 | 0.819 |
| 184 | Positive | 0.626 | 0.500 |
| 202 | Positive | 0.651 | 0.517 |
| 93 | Equivocal | 0.832 | 0.536 |
| 188 | Equivocal | 0.299 | 0.232 |
| 63 | Negative | 0.315 | 0.177 |

Of the seven specimens that are positive for HCMV IgM antibody by the consensus assays and by the "AxSYM" HCMV IgM assay described in U.S. Ser. No. 08/765,856, five of these specimens are positive and two are equivocal for HCMV IgM antibody by the "AxSYM" HCMV IgM assay described in this invention. This is in contrast to the reduced AH antigen version of the assay (see Example 2, TABLE II), where only one of the seven specimens were determined to be positive for HCMV IgM antibody. In conclusion, the "AxSYM" HCMV IgM assay of this invention has significantly improved diagnostic assay specificity with comparable diagnostic assay sensitivity over the previous "AxSYM" HCMV IgM assay described in U.S. Ser. No 08/765,856.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for detection of human cytomegalovirus infection comprising the steps of:
   (a) providing a mixture comprising (1) a solid phase containing at least one fusion protein, said at least one fusion protein comprising at least one peptide having at least one epitope of human cytomegalovirus that specifically binds to human cytomegalovirus-specific IgM, said at least one fusion protein comprising peptides A1C2 and F3, (2) a patient specimen, and (3) peptides A1C2 and F3;
   (b) allowing IgM antibodies to human cytomegalovirus to specifically bind to said at least one fusion protein and to the peptides A1C2 and F3;
   (c) adding an IgM conjugate to detect IgM antibodies specifically bound to said at least one fusion protein contained on said solid phase; and
   (d) determining the level of IgM antibodies to human cytomegalovirus in the patient specimen, wherein the amount of said peptides A1C2 and F3 is sufficient to bind low levels of human cytomegalovirus-specific IgM antibody present in patient specimens not indicative of acute or recent human cytomegalovirus infection yet not so great that said amount of said peptides A1C2 and F3 binds medium to high levels of human cytomegalovirus-specific IgM antibody present in patient specimens indicative of acute or recent human cytomegalovirus infection.

2. The method of claim 1, wherein said at least one epitope of human cytomegalovirus is present in pp150.

3. The method of claim 2, wherein said solid phase contains the fusion protein H10 of pp52/A1 C2 of pp150 (SEQ ID NO: 5)/F3 of pp150 (SEQ ID NO: 6) of human cytomegalovirus.

4. The method of claim 2, wherein the peptides comprise A1C2 (SEQ ID NO: 5) and F3 (SEQ ID NO: 6) of pp150 of human cytomegalovirus.

5. The method of claim 1, wherein said solid phase comprises a microparticle.

6. The method of claim 1, wherein said solid phase comprises a strip of material.

7. The method of claim 1, wherein the concentration of each of said at least one peptide ranges from about 1 µg/ml to about 25 µg/ml.

8. A reagent suitable for detection of human cytomegalovirus infection comprising microparticles coated with at least one fusion protein, said at least one fusion protein comprising at least one peptide having at least one epitope of human cytomegalovirus that specifically binds to human cytomegalovirus-specific IgM, said at least one fusion protein comprising peptides A1C2 and F3, said microparticles suspended in a diluent containing peptides A1C2 and F3, wherein the amount of said peptides A1C2 and F3 is sufficient to bind low levels of human cytomegalovirus-specific IgM antibody present in patient specimens not indicative of acute or recent human cytomegalovirus infection yet not so great that the amount of said peptides A1C2 and F3 binds medium to high levels of human cytomegalovirus-specific IgM antibody present in patient specimens indicative of acute or recent human cytomegalovirus infection.

9. The reagent of claim 8, wherein said at least one epitope of pp150 of human cytomegalovirus that specifically binds to human cytomegalovirus-specific IgM further includes the fusion protein H10 of pp52.

10. The reagent of claim 8, wherein said at least one peptide comprises the peptides A1C2 (SEQ ID NO: 5)and F3 (SEQ ID NO: 6).

11. The reagent of claim 8, wherein the concentration of each of said at least one peptide ranges from about 1 µg/ml to about 25 µg/ml.

12. A reagent containing peptides A1C2 and F3, wherein the amount of said peptides A1C2 and F3 is sufficient to bind low levels of human cytomegalovirus-specific IgM antibody present in patient specimens not indicative of acute or recent human cytomegalovirus infection yet not so great that the amount of said peptides A1C2 and F3 binds medium to high levels of human cytomegalovirus-specific IgM antibody present in patient specimens indicative of acute or recent human cytomegalovirus infection.

13. The reagent of claim 12, wherein said at least one peptide comprises the peptides A1C2 (SEQ ID NO: 5)and F3 (SEQ ID NO: 6).

14. A kit suitable for detection of human cytomegalovirus infection comprising:

(a) microparticles coated with at least one fusion protein, said at least one fusion Protein comprising at least one peptide having at least one epitope of human cytomegalovirus that specifically binds to human cytomegalovirus-specific IgM suspended in a diluent containing at least one peptide capable of specifically binding IgM antibodies to human cytomegalovirus, said at least one fusion protein comprising peptides A1C2 and F3, wherein the amount of said peptides A1C2 and F3 is sufficient to bind low levels of human cytomegalovirus-specific IgM antibody present in patient specimens not indicative of acute or recent human cytomegalovirus infection yet not so great that the amount of said peptides A1C2 and F3 binds medium to high levels of human cytomegalovirus-specific IgM antibody present in patient specimens indicative of acute or recent human cytomegalovirus infection;

(b) IgM conjugate in a diluent; and (c) buffered diluent containing a blocking agent.

15. The kit of claim 14, wherein said at least a portion of human cytomegalovirus is pp150.

16. The kit of claim 14, wherein said human cytomegalovirus comprises purified recombinant human cytomegalovirus antigen.

17. The kit of claim 14, wherein said at least one peptide comprises the peptides A1C2 (SEQ ID NO: 5)and F3 (SEQ ID NO: 6).

18. The kit of claim 14, wherein said diluent in (a) is a buffered sucrose/calf serum diluent.

19. The kit of claim 14, wherein said conjugate in (b) is an anti-human IgM enzyme conjugate.

20. The kit of claim 14, wherein said conjugate in (b) is an anti-human IgM fluorescent conjugate.

21. The kit of claim 14, wherein said conjugate in (b) is an anti-human IgM chemilumunescent conjugate.

22. The kit of claim 14, wherein the diluent in (b) is buffered calf serum.

23. The kit of claim 14, wherein the blocking agent in (c) is calf serum.

24. A kit suitable for detection of human cytomegalovirus infection comprising:

(a) a strip of material containing human cytomegalovirus antigens;

(b) sample dilution buffer containing at least one peptide capable of specifically binding IgM antibodies to human cytomegalovirus-, wherein the amount of said at least one peptide capable of specifically binding IgM antibodies to human cytomegalovirus is sufficient to bind low levels of human cytomegalovirus-specific IgM antibody present in patient specimens not indicative of acute or recent human cytomegalovirus infection yet not so great that said at least one peptide capable of specifically binding IgM antibodies to human cytomegalovirus binds medium to high levels of human cytomegalovirus-specific IgM antibody present in patient specimens indicative of acute or recent human cytomegalovirus infection;

(c) IgM conjugate in a diluent;

(d) buffered wash solution; and (e) color development reagent.

25. The kit of claim 24, wherein said at least one peptide comprises the peptides A1C2 (SEQ ID NO: 5) and F3 (SEQ ID NO: 6).

26. The kit of claim 24, wherein said strip of material comprises nitrocellulose.

27. The kit of claim 24, wherein said human cytomegalovirus antigens; comprise purified viral and recombinant human cytomegalovirus antigens.

28. The kit of claim 24, wherein said conjugate in (c) is an anti-human IgM enzyme conjugate.

29. The kit of claim 24, wherein said conjugate in (c) is an anti-human IgM fluorescent conjugate.

30. The kit of claim 24, wherein said conjugate in (c) is an anti-human IgM chemilumunescent conjugate.

* * * * *

UNITED STATES PATENT AND TRADEMARK OFFICE
CERTIFICATE OF CORRECTION

PATENT NO. : 6,177,241 B1
DATED : January 23, 2001
INVENTOR(S) : Gregory T. Maine It is certified that error appears in the above-identified patent and that said Letters Patent is hereby corrected as shown below:

Column 51,
Line 53, replace "one fusion Protein comprising" with -- one fusion protein comprising --.

Column 52,
Line 56, replace "cytomegalovirus antigens;" with -- cytomegalovirus antigens --.

Signed and Sealed this

Twelfth Day of March, 2002

Attest:

JAMES E. ROGAN
*Attesting Officer*  *Director of the United States Patent and Trademark Office*

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
      (A) LENGTH: 908 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: HUMAN CYTOMEGALOVIRUS (HCMV)

(vii) IMMEDIATE SOURCE:
      (B) CLONE: pROS (ix) FEATURE:
      (A) NAME/KEY: CDS
      (B) LOCATION:1..900

(x) PUBLICATION INFORMATION:
      (A) AUTHORS: RIPALTI, Alessandro
         ET AL.,
      (B) TITLE: CONSTRUCTION OF A POLYEPITOPE FUSION ANTIGEN
         OF HUMAN CYTOMEGALOVIRUS ppUL32; REACTIVITY WITH
         HUMAN ANTIBODIES
      (C) JOURNAL: J. Clin. Microbiol.
      (D) VOLUME: 32
      (F) PAGES: 358-363
      (G) DATE: 1994
      (K) RELEVANT RESIDUES IN SEQ ID NO: 1: FROM 233 TO 900

(x) PUBLICATION INFORMATION:
      (A) AUTHORS: RIPALTI, Alessandro
         ET AL.,
      (B) TITLE: Procaryotic expression of a large fragment of
         the most antigenic cytomegalovirus DNA-binding
         protein (ppUL44) and its reactivity with human
         antibodies.
      (C) JOURNAL: J. Virol.Methods

```
        (D) VOLUME: 46
        (F) PAGES: 39-50
        (G) DATE: 1994
        (K) RELEVANT RESIDUES IN SEQ ID NO: 1: FROM 1 TO 232

(x) PUBLICATION INFORMATION:
        (H) DOCUMENT NUMBER: EP 0262531 B1
        (I) FILING DATE: 05-JUN-1987
        (J) PUBLICATION DATE: 02-DEC-1992

(xi) SEQUENCE DESCRIPTION: SEQ ID NO: 1:

GAA TTC ACA GCC AAT AAC CGC GTC AGT TTC CAC GGC GTA AAA AAC ATG        48
Glu Phe Thr Ala Asn Asn Arg Val Ser Phe His Gly Val Lys Asn Met
 1               5                  10                  15

CGT ATC AAC GTG CAG CTG AAG AAC TTC TAC CAG ACG CTG CTC AAT TGC        96
Arg Ile Asn Val Gln Leu Lys Asn Phe Tyr Gln Thr Leu Leu Asn Cys
             20                  25                  30

GCC GTC ACC AAA CTA CCG TGC ACG CTG CGT ATA GTT ACG GAG CAC GAC       144
Ala Val Thr Lys Leu Pro Cys Thr Leu Arg Ile Val Thr Glu His Asp
         35                  40                  45

ACG CTG TTG TAC GTG GCC AGC CGC AAC GGT CTG TTC GCC GTG GAG AAC       192
Thr Leu Leu Tyr Val Ala Ser Arg Asn Gly Leu Phe Ala Val Glu Asn
     50                  55                  60

TTT CTC ACC GAG GAA CCT TTC CAG CGT GGC GAT CCC TTC GAC AAA AAT       240
Phe Leu Thr Glu Glu Pro Phe Gln Arg Gly Asp Pro Phe Asp Lys Asn
 65                  70                  75                  80

TAC GTC GGG AAC AGC GGC AAG TCG CGT GGC GGC GGC GGT GGC GGC           288
Tyr Val Gly Asn Ser Gly Lys Ser Arg Gly Gly Gly Gly Gly Gly
                 85                  90                  95

AGC CTC TCT TCG CTG GCC AAT GCC GGC GGT CTG CAC GAC GAC GGC CCG       336
Ser Leu Ser Ser Leu Ala Asn Ala Gly Gly Leu His Asp Asp Gly Pro
                100                 105                 110

GGT CTG GAT AAC GAT CTC ATG AAC GAG CCC ATG GGT CTC GGC GGT CTG       384
Gly Leu Asp Asn Asp Leu Met Asn Glu Pro Met Gly Leu Gly Gly Leu
        115                 120                 125

GGA GGA GGT GGC GGC GGT GGC GGC AAG AAG CAC GAC CGC GGT GGC GGC       432
Gly Gly Gly Gly Gly Gly Gly Gly Lys Lys His Asp Arg Gly Gly Gly
    130                 135                 140

GGT GGT TCC GGT ACG CGG AAA ATG AGC AGC GGT GGC GGC GGC GGT GAT       480
Gly Gly Ser Gly Thr Arg Lys Met Ser Ser Gly Gly Gly Gly Gly Asp
145                 150                 155                 160

CAC GAT CAC GGT CTT TCC TCC AAG GAA AAA TAC GAG CAG CAC AAG ATC       528
His Asp His Gly Leu Ser Ser Lys Glu Lys Tyr Glu Gln His Lys Ile
                165                 170                 175

ACC AGT TAC CTG ACG TCC AAA GGT GGA TCG GGC GGC GGC GGA GGA GGA       576
Thr Ser Tyr Leu Thr Ser Lys Gly Gly Ser Gly Gly Gly Gly Gly Gly
                180                 185                 190

GGA GGC GGC GGT TTG GAT CGC AAC TCC GGC AAT TAC TTC AAC GAC GCG       624
Gly Gly Gly Gly Leu Asp Arg Asn Ser Gly Asn Tyr Phe Asn Asp Ala
            195                 200                 205

AAA GAG GAG AGC GAC AGC GAG GAT TCT GTA ACG TTC GAG TTC GTC CCT       672
Lys Glu Glu Ser Asp Ser Glu Asp Ser Val Thr Phe Glu Phe Val Pro
    210                 215                 220

AAC ACC AAG AAG CAA AAG TGC GGC ACG CCG ACG CCT GTC AAT CCT TCC       720
Asn Thr Lys Lys Gln Lys Cys Gly Thr Pro Thr Pro Val Asn Pro Ser
225                 230                 235                 240

ACG GCC CCC GCT CCG GCC CCG ACA CCT ACC TTC GCG AAG CTT CAG GAA       768
Thr Ala Pro Ala Pro Ala Pro Thr Pro Thr Phe Ala Lys Leu Gln Glu
                245                 250                 255

TTC GGA TCG TCG CCC CAG AAG AGC GGT ACG GGG CCG CAA CCG GGT TCT       816
Phe Gly Ser Ser Pro Gln Lys Ser Gly Thr Gly Pro Gln Pro Gly Ser
                260                 265                 270
```

```
GCC GGC ATG GGG GGC GCC AAA ACG CCG TCG GAC GCC GTG CAG AAC ATC       864
Ala Gly Met Gly Gly Ala Lys Thr Pro Ser Asp Ala Val Gln Asn Ile
            275                 280                 285

CTC CAA AAG ATC GAG AAG ATT AAG AAC ACG GAG GAA TAGAATTC              908
Leu Gln Lys Ile Glu Lys Ile Lys Asn Thr Glu Glu
    290                 295                 300

(2) INFORMATION FOR SEQ ID NO: 2:

(i) SEQUENCE CHARACTERISTICS:
        (A) LENGTH: 300 amino acids
        (B) TYPE: amino acid
        (D) TOPOLOGY: linear (ii) MOLECULE TYPE: protein (xi) SEQUENCE DESCRIPTION: SEQ ID NO: 2:

Glu Phe Thr Ala Asn Asn Arg Val Ser Phe His Gly Val Lys Asn Met
  1               5                  10                  15

Arg Ile Asn Val Gln Leu Lys Asn Phe Tyr Gln Thr Leu Leu Asn Cys
             20                  25                  30

Ala Val Thr Lys Leu Pro Cys Thr Leu Arg Ile Val Thr Glu His Asp
             35                  40                  45

Thr Leu Leu Tyr Val Ala Ser Arg Asn Gly Leu Phe Ala Val Glu Asn
     50                  55                  60

Phe Leu Thr Glu Glu Pro Phe Gln Arg Gly Asp Pro Phe Asp Lys Asn
 65                  70                  75                  80

Tyr Val Gly Asn Ser Gly Lys Ser Arg Gly Gly Gly Gly Gly Gly Gly
                 85                  90                  95

Ser Leu Ser Ser Leu Ala Asn Ala Gly Gly Leu His Asp Asp Gly Pro
                100                 105                 110

Gly Leu Asp Asn Asp Leu Met Asn Glu Pro Met Gly Leu Gly Gly Leu
                115                 120                 125

Gly Gly Gly Gly Gly Gly Gly Lys Lys His Asp Arg Gly Gly Gly
    130                 135                 140

Gly Gly Ser Gly Thr Arg Lys Met Ser Ser Gly Gly Gly Gly Asp
145                 150                 155                 160

His Asp His Gly Leu Ser Ser Lys Glu Lys Tyr Glu Gln His Lys Ile
                165                 170                 175

Thr Ser Tyr Leu Thr Ser Lys Gly Gly Ser Gly Gly Gly Gly Gly
            180                 185                 190

Gly Gly Gly Gly Leu Asp Arg Asn Ser Gly Asn Tyr Phe Asn Asp Ala
    195                 200                 205

Lys Glu Glu Ser Asp Ser Glu Asp Ser Val Thr Phe Glu Phe Val Pro
    210                 215                 220

Asn Thr Lys Lys Gln Lys Cys Gly Thr Pro Thr Pro Val Asn Pro Ser
225                 230                 235                 240

Thr Ala Pro Ala Pro Ala Pro Thr Pro Thr Phe Ala Lys Leu Gln Glu
            245                 250                 255

Phe Gly Ser Ser Pro Gln Lys Ser Gly Thr Gly Pro Gln Pro Gly Ser
            260                 265                 270

Ala Gly Met Gly Gly Ala Lys Thr Pro Ser Asp Ala Val Gln Asn Ile
            275                 280                 285

Leu Gln Lys Ile Glu Lys Ile Lys Asn Thr Glu Glu
    290                 295                 300
```

(2) INFORMATION FOR SEQ ID NO: 3:

(i) SEQUENCE CHARACTERISTICS:
        (A) LENGTH: 906 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (v) FRAGMENT TYPE: internal (vi) ORIGINAL SOURCE:
       (A) ORGANISM: Human Cytomegalovirus (HCMV)

(vii) IMMEDIATE SOURCE:
       (B) CLONE: pCMV-27

(ix) FEATURE:
       (A) NAME/KEY: CDS
       (B) LOCATION:1..906

(x) PUBLICATION INFORMATION:
       (H) DOCUMENT NUMBER: EP 0262531 B1
       (I) FILING DATE: 05-JUN-1987
       (J) PUBLICATION DATE: 02-DEC-1992

(xi) SEQUENCE DESCRIPTION: SEQ ID NO: 3:

```
ACG CCG ACG CCT GTC AAT CCT TCC ACG GCC CCC GCT CCG GCC CCG ACA        48
Thr Pro Thr Pro Val Asn Pro Ser Thr Ala Pro Ala Pro Ala Pro Thr
            305                 310                 315

CCT ACC TTC GCG AAG CTT CAG GAA TTC GGA TCG TCG CCC CAG AAG AGC        96
Pro Thr Phe Ala Lys Leu Gln Glu Phe Gly Ser Ser Pro Gln Lys Ser
            320                 325                 330

GGT ACG GGG CCG CAA CCG GGT TCT GCC GGC ATG GGG GGC GCC AAA ACG       144
Gly Thr Gly Pro Gln Pro Gly Ser Ala Gly Met Gly Gly Ala Lys Thr
            335                 340                 345

CCG TCG GAC GCC GTG CAG AAC ATC CTC CAA AAG ATC GAG AAG ATT AAG       192
Pro Ser Asp Ala Val Gln Asn Ile Leu Gln Lys Ile Glu Lys Ile Lys
            350                 355                 360

AAC ACG GAG GAA CTT CAG GAA TTC ACA GCC AAT AAC CGC GTC AGT TTC       240
Asn Thr Glu Glu Leu Gln Glu Phe Thr Ala Asn Asn Arg Val Ser Phe
365                 370                 375                 380

CAC GGC GTA AAA AAC ATG CGT ATC AAC GTG CAG CTG AAG AAC TTC TAC       288
His Gly Val Lys Asn Met Arg Ile Asn Val Gln Leu Lys Asn Phe Tyr
            385                 390                 395

CAG ACG CTG CTC AAT TGC GCC GTC ACC AAA CTA CCG TGC ACG CTG CGT       336
Gln Thr Leu Leu Asn Cys Ala Val Thr Lys Leu Pro Cys Thr Leu Arg
            400                 405                 410

ATA GTT ACG GAG CAC GAC ACG CTG TTG TAC GTG GCC AGC CGC AAC GGT       384
Ile Val Thr Glu His Asp Thr Leu Leu Tyr Val Ala Ser Arg Asn Gly
            415                 420                 425

CTG TTC GCC GTG GAG AAC TTT CTC ACC GAG GAA CCT TTC CAG CGT GGC       432
Leu Phe Ala Val Glu Asn Phe Leu Thr Glu Glu Pro Phe Gln Arg Gly
            430                 435                 440

GAT CCC TTC GAC AAA AAT TAC GTC GGG AAC AGC GGC AAG TCG CGT GGC       480
Asp Pro Phe Asp Lys Asn Tyr Val Gly Asn Ser Gly Lys Ser Arg Gly
445                 450                 455                 460

GGC GGT GGT GGC GGC AGC CTC TCT TCG CTG GCC AAT GCC GGC GGT           528
Gly Gly Gly Gly Gly Gly Ser Leu Ser Ser Leu Ala Asn Ala Gly Gly
            465                 470                 475

CTG CAC GAC GAC GGC CCG GGT CTG GAT AAC GAT CTC ATG AAC GAG CCC       576
Leu His Asp Asp Gly Pro Gly Leu Asp Asn Asp Leu Met Asn Glu Pro
```

```
ATG GGT CTC GGC GGT CTG GGA GGA GGT GGC GGC GGT GGC GGC AAG AAG      624
Met Gly Leu Gly Gly Leu Gly Gly Gly Gly Gly Gly Gly Gly Lys Lys
        495                 500                 505

CAC GAC CGC GGT GGC GGC GGT GGT TCC GGT ACG CGG AAA ATG AGC AGC      672
His Asp Arg Gly Gly Gly Gly Gly Ser Gly Thr Arg Lys Met Ser Ser
510                 515                 520

GGT GGC GGC GGC GGT GAT CAC GAT CAC GGT CTT TCC TCC AAG GAA AAA      720
Gly Gly Gly Gly Gly Asp His Asp His Gly Leu Ser Ser Lys Glu Lys
525                 530                 535                 540

TAC GAG CAG CAC AAG ATC ACC AGT TAC CTG ACG TCC AAA GGT GGA TCG      768
Tyr Glu Gln His Lys Ile Thr Ser Tyr Leu Thr Ser Lys Gly Gly Ser
            545                 550                 555

GGC GGC GGC GGA GGA GGA GGA GGC GGC GGT TTG GAT CGC AAC TCC GGC      816
Gly Gly Gly Gly Gly Gly Gly Gly Gly Gly Leu Asp Arg Asn Ser Gly
                560                 565                 570

AAT TAC TTC AAC GAC GCG AAA GAG GAG AGC GAC AGC GAG GAT TCT GTA      864
Asn Tyr Phe Asn Asp Ala Lys Glu Glu Ser Asp Ser Glu Asp Ser Val
        575                 580                 585

ACG TTC GAG TTC GTC CCT AAC ACC AAG AAG CAA AAG TGC GGC              906
Thr Phe Glu Phe Val Pro Asn Thr Lys Lys Gln Lys Cys Gly
        590                 595                 600
```

(2) INFORMATION FOR SEQ ID NO: 4:

(i) SEQUENCE CHARACTERISTICS:
        (A) LENGTH: 302 amino acids
        (B) TYPE: amino acid
        (D) TOPOLOGY: linear (ii) MOLECULE TYPE: protein (xi) SEQUENCE DESCRIPTION: SEQ ID NO: 4:

```
Thr Pro Thr Pro Val Asn Pro Ser Thr Ala Pro Ala Pro Ala Pro Thr
 1               5                  10                  15

Pro Thr Phe Ala Lys Leu Gln Glu Phe Gly Ser Ser Pro Gln Lys Ser
            20                  25                  30

Gly Thr Gly Pro Gln Pro Gly Ser Ala Gly Met Gly Gly Ala Lys Thr
        35                  40                  45

Pro Ser Asp Ala Val Gln Asn Ile Leu Gln Lys Ile Glu Lys Ile Lys
 50                  55                  60

Asn Thr Glu Glu Leu Gln Glu Phe Thr Ala Asn Asn Arg Val Ser Phe
 65                  70                  75                  80

His Gly Val Lys Asn Met Arg Ile Asn Val Gln Leu Lys Asn Phe Tyr
                85                  90                  95

Gln Thr Leu Leu Asn Cys Ala Val Thr Lys Leu Pro Cys Thr Leu Arg
            100                 105                 110

Ile Val Thr Glu His Asp Thr Leu Leu Tyr Val Ala Ser Arg Asn Gly
            115                 120                 125

Leu Phe Ala Val Glu Asn Phe Leu Thr Glu Pro Phe Gln Arg Gly
        130                 135                 140

Asp Pro Phe Asp Lys Asn Tyr Val Gly Asn Ser Gly Lys Ser Arg Gly
145                 150                 155                 160

Gly Gly Gly Gly Gly Ser Leu Ser Ser Leu Ala Asn Ala Gly Gly
                165                 170                 175

Leu His Asp Asp Gly Pro Gly Leu Asp Asn Asp Leu Met Asn Glu Pro
            180                 185                 190

Met Gly Leu Gly Gly Leu Gly Gly Gly Gly Gly Gly Gly Lys Lys
```

```
                195                 200                 205
His Asp Arg Gly Gly Gly Gly Ser Gly Thr Arg Lys Met Ser Ser
    210                 215                 220

Gly Gly Gly Gly Gly Asp His Asp His Gly Leu Ser Ser Lys Glu Lys
225                 230                 235                 240

Tyr Glu Gln His Lys Ile Thr Ser Tyr Leu Thr Ser Lys Gly Gly Ser
                245                 250                 255

Gly Gly Gly Gly Gly Gly Gly Gly Leu Asp Arg Asn Ser Gly
            260                 265                 270

Asn Tyr Phe Asn Asp Ala Lys Glu Glu Ser Asp Ser Glu Asp Ser Val
                275                 280                 285

Thr Phe Glu Phe Val Pro Asn Thr Lys Lys Gln Lys Cys Gly
    290                 295                 300

(2) INFORMATION FOR SEQ ID NO:5:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:5:

Thr Pro Thr Pro Val Asn Pro Ser Thr Ala Pro Ala Pro Ala Pro Thr
1               5                   10                  15

Pro Thr Phe Ala
        20

(2) INFORMATION FOR SEQ ID NO:6:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:6:

Gly Ser Ser Pro Gln Lys Ser Gly Thr Gly Pro Gln Pro Gly Ser Ala
1               5                   10                  15

Gly Met Gly Gly Ala Lys Thr Pro Ser Asp Ala Val Gln Asn Ile Leu
            20                  25                  30

Gln Lys Ile Glu Lys Ile Lys Asn Thr Glu Glu
        35                  40

(2) INFORMATION FOR SEQ ID NO:7:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:7:

Lys Leu Gln Glu Phe
1               5

(2) INFORMATION FOR SEQ ID NO:8:
```

(i) SEQUENCE CHARACTERISTICS:
       (A) LENGTH: 30 base pairs
       (B) TYPE: nucleic acid
       (C) STRANDEDNESS: single
       (D) TOPOLOGY: linear (xi) SEQUENCE DESCRIPTION: SEQ ID NO:8:

GAATTCACAG CCAATAACCG CGTCAGTTTC                                    30

(2) INFORMATION FOR SEQ ID NO:9:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (xi) SEQUENCE DESCRIPTION: SEQ ID NO:9:

AGGCGTCGGC GTGCCGCACT TTTGCTTCTT GGTGTT                             36

(2) INFORMATION FOR SEQ ID NO:10:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (xi) SEQUENCE DESCRIPTION: SEQ ID NO:10:

CAAAAGTGCG GCACGCCGAC GCCTGTCAAT CCTTCC                             36

(2) INFORMATION FOR SEQ ID NO:11:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (xi) SEQUENCE DESCRIPTION: SEQ ID NO:11:

GAATTCCTAT TCCTCCGTGT TCTTAATCTT                                    30

(2) INFORMATION FOR SEQ ID NO:12:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (xi) SEQUENCE DESCRIPTION: SEQ ID NO:12:

GGATAACAAT TGGGCATCCA GTAAGGAGGT                                    30

(2) INFORMATION FOR SEQ ID NO:13:

(i) SEQUENCE CHARACTERISTICS:
       (A) LENGTH: 106 base pairs
       (B) TYPE: nucleic acid
       (C) STRANDEDNESS: single
       (D) TOPOLOGY: linear (xi) SEQUENCE DESCRIPTION: SEQ ID NO:13:

AGGATGCGGA TCCCCGATCT CGACCCGTCG ACGAATTCGA GCTCGGTACC CGGGGATCCT    60

CTAGACTGCA GGCATGCTAA GTAAGTAGAT CGGGAATTCA CATCCG                  106

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:14:

CCCGCGCGCT ACGCGTCGAC GCGTCTGCCC                                    30

(2) INFORMATION FOR SEQ ID NO:15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:15:

CCCGCGCGCT ACGCGACGTC GCGTCTGCCC                                    30

(2) INFORMATION FOR SEQ ID NO:16:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: Peptide (xi) SEQUENCE DESCRIPTION: SEQ ID NO:16:

Pro Ala Arg Tyr Ala Ser Thr Arg Leu Pro
1               5                   10

(2) INFORMATION FOR SEQ ID NO:17:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: Peptide (xi) SEQUENCE DESCRIPTION: SEQ ID NO:17:

Pro Ala Arg Tyr Ala Thr Ser Arg Leu Pro
1               5                   10